United States Patent
Neel et al.

(10) Patent No.: US 6,189,370 B1
(45) Date of Patent: *Feb. 20, 2001

(54) FLUID DOSE, FLOW AND COAGULATION SENSOR FOR MEDICAL INSTRUMENT

(75) Inventors: Gary T. Neel; James R. Parker, both of Indianapolis; Rick L. Collins, Cicero; David E. Storvick, Indianapolis; Charles L. Thomeczek, Jr., Fishers; William J. Murphy, Cicero; George R. Lennert, Fishers; Morris J. Young; Daniel L. Kennedy, both of Indianapolis, all of IN (US)

(73) Assignee: Roche Diagnostics Corporation, Indianapolis, IN (US)

(*) Notice: Under 35 U.S.C. 154(b), the term of this patent shall be extended for 0 days.

This patent is subject to a terminal disclaimer.

(21) Appl. No.: 09/098,708

(22) Filed: Jun. 17, 1998

Related U.S. Application Data

(63) Continuation of application No. 08/623,872, filed on Mar. 29, 1996, now Pat. No. 5,789,664, which is a continuation of application No. 08/114,913, filed on Aug. 31, 1993, now Pat. No. 5,522,255.

(51) Int. Cl.[7] .................................................. G01N 21/03
(52) U.S. Cl. .......................... 73/53.001; 356/39; 422/73; 436/69; 73/64.43
(58) Field of Search .................................. 600/368, 369; 356/39–41; 73/53.01, 64.43; 422/73; 436/69

(56) References Cited

U.S. PATENT DOCUMENTS

| | | |
|---|---|---|
| Re. 27,866 | 1/1974 | Adler . |
| Re. 28,009 | 5/1974 | Vicario . |
| 1,529,811 | 3/1925 | Priest . |
| 2,574,359 | 11/1951 | Thomas . |
| 2,625,817 | 1/1953 | Oppenauer . |
| 3,593,568 | 7/1971 | Schmitz et al. . |
| 3,635,678 | 1/1972 | Seitz et al. . |
| 3,656,073 | 4/1972 | Wood et al. . |
| 3,674,012 | 7/1972 | Sage . |
| 3,695,842 | 10/1972 | Mintz . |
| 3,699,437 | 10/1972 | Ur . |
| 3,752,443 | 8/1973 | Lichtenstein . |
| 3,754,866 | 8/1973 | Ritchie et al. . |

(List continued on next page.)

FOREIGN PATENT DOCUMENTS

| | | |
|---|---|---|
| 0 150 111 A2 | 7/1985 | (EP) . |
| 0 332 110 A2 | 9/1989 | (EP) . |
| 0 394 041 A2 | 10/1990 | (EP) . |
| 3-127248 | 5/1981 | (JP) . |
| 56055543 | 5/1981 | (JP) . |
| WO 89/10788 | 11/1989 | (WO) . |
| WO 92/01065 | 1/1992 | (WO) . |

OTHER PUBLICATIONS

Database WPI, Week 8547, Derwent Publications Ltd., London, G13; AN 85–259416; SU–A–1 157 456 (Kvant Trust); May 23, 1985; abstract.

*Primary Examiner*—Robert L. Nasser
(74) *Attorney, Agent, or Firm*—Barnes & Thornburg

(57) ABSTRACT

An instrument for determining a characteristic of a biological fluid or a control includes a radiation-reflective surface, a first source for irradiating the surface, and a first detector for detecting radiation reflected from the surface. A cuvette for use with the instrument holds a sample of the biological fluid or control the characteristic of which is to be determined. The cuvette has two opposed walls substantially transparent to the source radiation and reflected radiation. The first source and first detector are disposed adjacent a first one of said two opposed walls and the radiation reflective surface is disposed adjacent a second of said two opposed walls.

8 Claims, 17 Drawing Sheets

U.S. PATENT DOCUMENTS

| | | |
|---|---|---|
| 3,821,643 | 6/1974 | Bostick et al. . |
| 3,833,864 | 9/1974 | Kiess et al. . |
| 3,836,333 | 9/1974 | Mintz . |
| 3,840,806 | 10/1974 | Stoner et al. . |
| 3,882,442 | 5/1975 | Hubbard . |
| 3,946,200 | 3/1976 | Juodikis . |
| 3,967,934 | 7/1976 | Seitz et al. . |
| 4,000,972 | 1/1977 | Braun et al. . |
| 4,014,650 | 3/1977 | Sigelmann . |
| 4,034,601 | 7/1977 | Geiger . |
| 4,056,708 | 11/1977 | Soodak et al. . |
| 4,058,254 | 11/1977 | Hallgreen . |
| 4,081,242 | 3/1978 | Girolami . |
| 4,083,363 | 4/1978 | Philpotr, Jr. . |
| 4,105,411 | 8/1978 | Biver . |
| 4,112,740 | 9/1978 | Brandestini . |
| 4,125,327 | 11/1978 | Margolis . |
| 4,201,470 | 5/1980 | Ehrly et al. . |
| 4,217,107 | 8/1980 | Saito et al. . |
| 4,252,536 | 2/1981 | Kishimoto et al. . |
| 4,316,383 | 2/1982 | Fruman et al. . |
| 4,388,823 | 6/1983 | Garnaud et al. . |
| 4,400,353 | 8/1983 | Meserol et al. . |
| 4,427,940 | 1/1984 | Hirama et al. . |
| 4,492,462 | 1/1985 | Pross et al. . |
| 4,497,774 | 2/1985 | Scordato . |
| 4,501,491 | 2/1985 | Breda et al. . |
| 4,532,414 | 7/1985 | Shah et al. . |
| 4,558,589 | 12/1985 | Hemmes . |
| 4,599,219 | 7/1986 | Cooper et al. . |
| 4,612,801 | 9/1986 | Girolami . |
| 4,639,611 | 1/1987 | Sticher . |
| 4,659,550 | 4/1987 | Schildknecht . |
| 4,720,787 | 1/1988 | Lipscomb . |
| 4,740,460 | 4/1988 | Sakata et al. . |
| 4,741,612 | 5/1988 | Birngruber et al. . |
| 4,752,449 | 6/1988 | Jackson et al. . |
| 4,756,884 | 7/1988 | Hillman et al. . |
| 4,835,505 | 5/1989 | Hattori et al. . |
| 4,849,340 | 7/1989 | Oberhardt . |
| 4,868,832 | 9/1989 | Marrington et al. . |
| 4,876,069 | 10/1989 | Jochimsen . |
| 4,940,958 | 7/1990 | Ootsuka . |
| 4,944,304 | 7/1990 | Nishina . |
| 4,951,171 | 8/1990 | Tran et al. . |
| 4,963,498 | 10/1990 | Hillman et al. . |
| 4,964,728 | 10/1990 | Kloth et al. . |
| 5,010,469 | 4/1991 | Bobry . |
| 5,014,031 | 5/1991 | Nusser . |
| 5,047,211 | 9/1991 | Sloane, Jr. et al. . |
| 5,053,199 | 10/1991 | Keiser et al. . |
| 5,072,610 | 12/1991 | Martinoli et al. . |
| 5,110,727 | 5/1992 | Oberhardt . |
| 5,114,860 | 5/1992 | Hayashi . |
| 5,117,324 | 5/1992 | Johnson, Jr. . |
| 5,120,510 | 6/1992 | Gourley et al. . |
| 5,138,872 | 8/1992 | Henderson . |
| 5,140,161 | 8/1992 | Hillman et al. . |
| 5,154,082 | 10/1992 | Mintz . |
| 5,156,974 | 10/1992 | Grossman et al. . |
| 5,167,145 | 12/1992 | Butler et al. . |
| 5,181,415 | 1/1993 | Esvan et al. . |
| 5,193,543 | 3/1993 | Yelderman . |
| 5,253,648 | 10/1993 | Walloch . |
| 5,258,719 | 11/1993 | Miura et al. . |
| 5,272,912 | 12/1993 | Katsuzaki . |
| 5,302,348 | 4/1994 | Cusack et al. . |
| 5,339,830 | 8/1994 | Blake, III . |
| 5,341,034 | 8/1994 | Matthews . |
| 5,350,676 | 9/1994 | Oberhardt et al. . |
| 5,427,920 | 6/1995 | Berndt et al. . |
| 5,436,978 | 7/1995 | Kasden . |
| 5,473,706 | 12/1995 | Bacus et al. . |

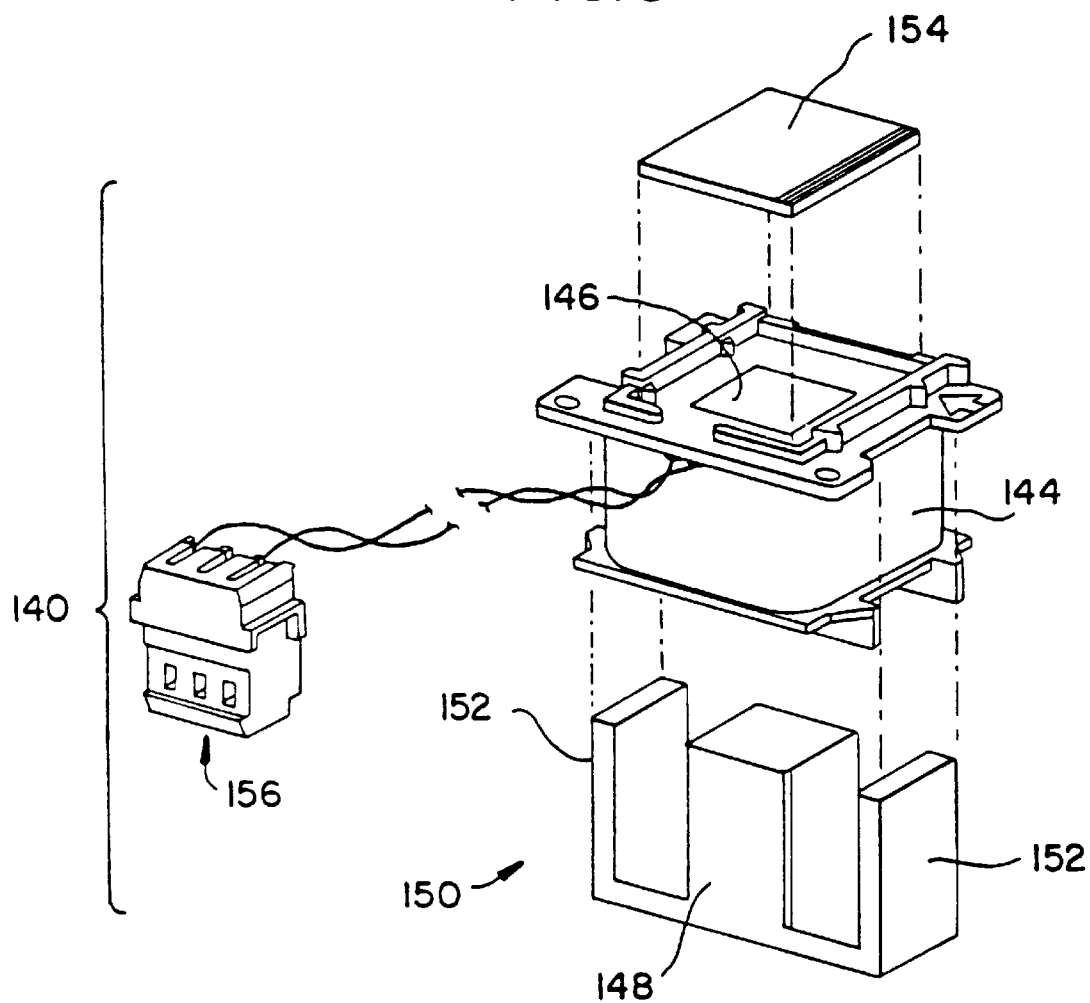

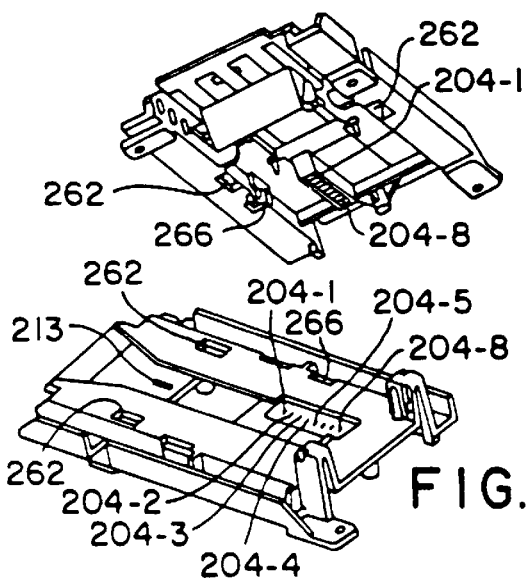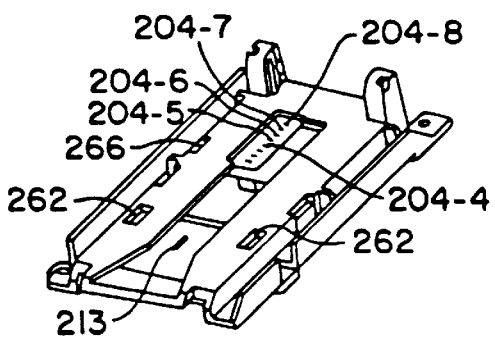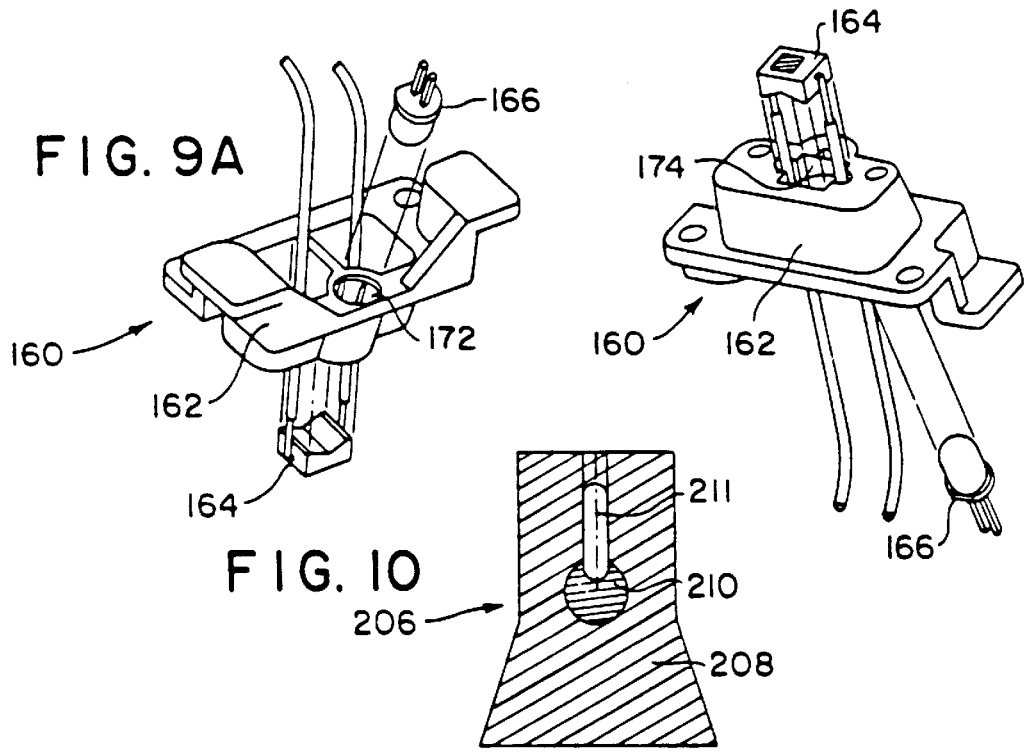

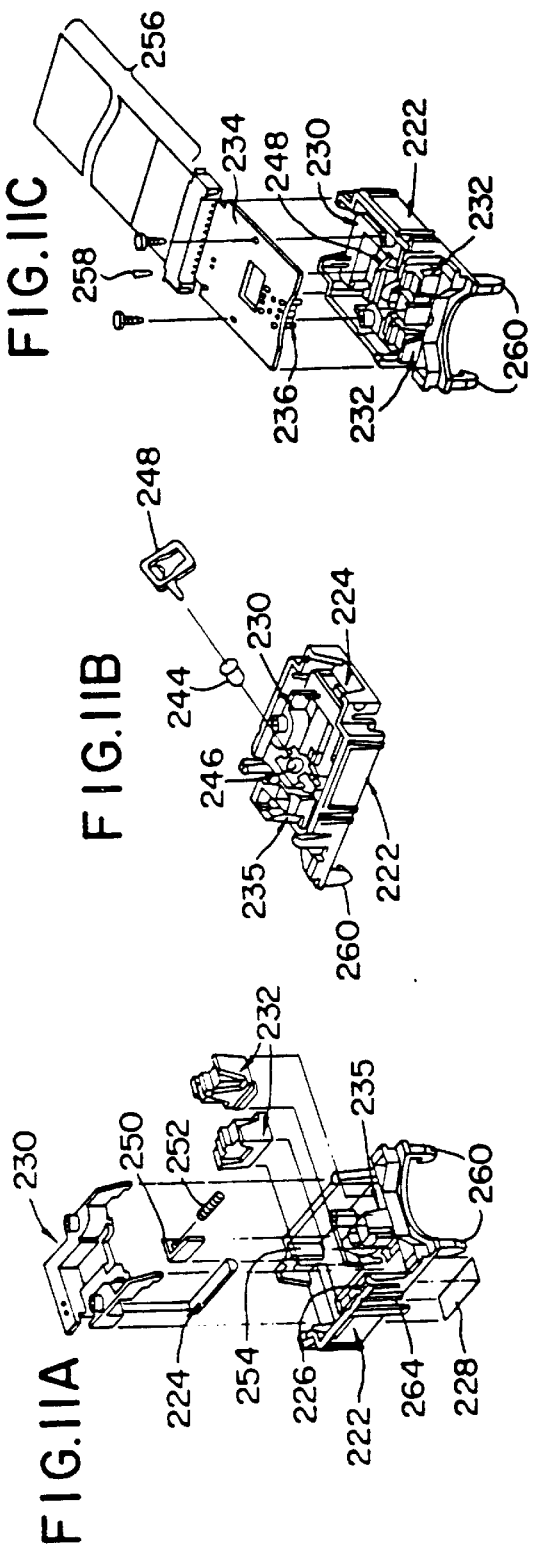

FLUID DOSE, FLOW AND COAGULATION SENSOR FOR MEDICAL INSTRUMENT

This is a continuation of U.S. Ser. No. 08/623,872, filed Mar. 29, 1996, now U.S. Pat. No. 5,789,664, assigned to the same assignee as this application. U.S. Ser. No. 08/623,872 is itself a continuation of U.S. Ser. No. 08/114,913, filed Aug. 31, 1993, now U.S. Pat. No. 5,522,255.

This is a related application to U.S. Ser. No. 08/114,915, titled ANALOG HEATER CONTROL FOR MEDICAL INSTRUMENT, U.S. Ser. No. 08/114,914, titled POWER SUPPLY MONITOR AND CONTROL FOR MEDICAL INSTRUMENT, U.S. Ser. No. 08/114,896, titled MAGNETIC SYSTEM FOR MEDICAL INSTRUMENT, U.S. Ser. No. 08/114,579, titled REAGENT AND METHOD OF ITS USE, and U.S. Ser. No. 08/114,897, titled METHOD AND APPARATUS FOR OPERATING A MEDICAL INSTRUMENT, all filed on the same date as this application and assigned to the same assignee, the disclosure of which is incorporated herein by reference.

This invention relates to method and apparatus for determining blood coagulation times.

Several methods are known for determining blood coagulation time. These include laser speckle methods, ultrasonic measurement methods, transmission direct clotting methods, ball and tilted cup direct clotting methods, and the methods illustrated in, for example, U.S. Pat. Nos.: 4,756,884; 4,849,340; 4,963,498; 5,110,727; and, 5,140,161. Many of these prior art methods do not measure blood coagulation times directly, and thus are subject to errors that can enter into indirect measurement processes. Many of these methods do not determine whether there is an adequate blood sample, and thus are subject to errors that can enter into processes which do not determine adequacy of the blood sample. Many of these methods do not distinguish between blood and control or test solutions, and thus are subject to errors that can enter into processes which do not determine whether a specimen being tested is blood or a control or test solution. Many of these methods do not accurately ascertain the start of a coagulation test, and thus are subject to errors that can enter into processes which do not ascertain accurately the start of a coagulation test. None of these methods combine the specimen heating function required to obtain accurate coagulation time test results with a radiation reflector for reflecting test parameters to a radiation detector.

According to the invention, a system is provided for determining coagulation time directly by a reflectance technique. According to an illustrative embodiment of the invention, a coagulation testing meter employs a combination of reflectance sensors and a sample application, start, fill and assay technique to determine coagulation time.

An easy-access, cleanable adapter can be opened by pushing a release button located on the front of the instrument. This provides for easy cleaning in the event that contamination occurs during the conduct of a test. The adapter top is hinged toward the back of the adapter and pops up in somewhat the same manner as a car hood when the release button is actuated. The adapter top has a flag that blocks a light path of an interrupt sensor to indicate when the top is closed in testing position.

A combination reagent heater and reflector includes an aluminum nitride heater plate which heats the reagent test strip to a controlled temperature and acts as an optical reflector for a start sensor, an adequate sample sensor, and an assay sensor. A sample sensor which reads through the clear bottom of a coagulation time test strip dictates the need for a heater plate that reflects light.

A sample application icon is a yellow dot that is viewed by the user through the clear bottom of the test strip to indicate to the user where to apply the sample, the coagulation time of which is to be determined.

A sample flow sensor detects that adequate sample has been applied to the test strip and identifies the type of sample, that is, control or blood, by the flow time signature. The flow time is calculated as the time difference between actuation of a flow sensor and actuation of a start sensor. This marks the sample type in the coagulation testing instrument's memory as a control test or a blood test. If the sample takes longer than an established time stored in read-only memory in the instrument to flow from the flow sensor to the start sensor, the instrument stores an indication that the sample volume is insufficient. The flow sensor is a reflective sensor that senses a composite net loss in signal as a result of change of index of refraction, scattering, and absorption differences between air (no sample applied) and sample (blood or control).

The start sensor detects when a sample enters the area of a test strip coated with a coagulation time measurement-assisting reagent. This activates a timer for timing the clotting process. The start sensor also is a reflective optical sensor that senses a composite net loss in signal as a result of change in index of refraction, scattering, and absorption differences between air and sample. An LED light source directs light through a clear strip to a heater plate, which reflects light back through the strip onto a photodetector.

An adequate sample sensor is only activated if a blood sample is detected within the established time stored in the read-only memory. The adequate sample sensor detects if the reagent area is covered by the sample. It also prevents the instrument from performing the test if the user applies a second dose of sample to the strip (double-dosing the strip), if the second dose is applied more than the established time after the first. The sample must flow from the start sensor through a fill optical read area of the instrument within the established time, or the instrument reports insufficient sample. The adequate sample sensor also is a reflective sensor that senses a composite net loss in signal as a result of change in index of refraction, scattering, and absorption differences between air and sample. An LED light source directs light through the clear strip to the heater plate, which reflects light back through the strip onto a photodetector.

An assay sensor outputs a signal that is proportional to the change in heater plate reflectance when modulated by spatial iron particle movement induced by a 2 Hz alternating electromagnetic field. An LED light source directs light through the clear strip to the heater plate, which reflects light back through the strip onto a photodetector. When the sample clots, the iron particles are restricted from moving. The change in the reflected light signal decreases. Data collection continues for a predetermined period of time stored in read-only memory. At the end of this predetermined period of time, the collected data is analyzed to determine the clotting time.

According to one aspect of the invention, an instrument for determining the coagulation time of blood, a blood fraction or a control comprises a radiation-reflective surface, a first source for irradiating the surface, and a first detector for detecting radiation reflected from the surface. A cuvette holds a sample of the blood, blood fraction or control the coagulation time of which is to be determined. The cuvette has two opposed walls substantially transparent to the source radiation and reflected radiation. The first source and first detector are disposed adjacent a first one of said two opposed walls and the radiation reflective surface is disposed adjacent a second of said two opposed walls.

According to another aspect of the invention, a method for determining the coagulation time of blood, a blood fraction or a control comprises irradiating a radiation-reflective surface through a cuvette for holding a sample of the blood, blood fraction or control the coagulation time of which is to be determined using a first radiation source, and detecting radiation reflected from the surface using a first radiation detector. The cuvette has two opposed walls substantially transparent to the source radiation and reflected radiation.

Illustratively, according to the invention, the instrument further comprises a second source for irradiating the cuvette and a second detector for detecting when a sample has been applied to a sample application point in the cuvette. The second detector detects radiation from the second radiation source transmitted through one of said two opposed walls of the cuvette, reflected by the sample and transmitted back through said one wall to the second detector.

Additionally, illustratively according to the invention, a third source irradiates the surface. The first detector detects radiation from the third source reflected from the surface. The third source is positioned to transmit radiation through said two opposed walls for reflection by the surface and transmission back through said two opposed walls to the first detector to indicate that a sample has reached a first point in the cuvette.

Further, illustratively according to the invention, a fourth source irradiates the surface. The first detector detects radiation from the fourth source reflected from the surface. The fourth source is positioned to transmit radiation through said two opposed walls for reflection by the surface and transmission back through said two opposed walls to the first detector to indicate that a sample has reached a second point in the cuvette.

Illustratively, according to the invention, the second point is downstream in the spread of the sample from the first point and the first point is downstream in the spread of the sample from the sample application point.

Additionally, according to the present invention, a heater is provided for maintaining the blood, blood fraction or control at a desired temperature. Means are provided for mounting the heater adjacent the surface. Means are provided to power the heater. Means are provided for monitoring the surface temperature and for feeding the monitored temperature back to the means for providing power to the heater.

Illustratively, the heater comprises an electrically resistive foil. The surface comprises a first radiation reflective surface of a plate. The plate further comprises a second surface opposite the first surface thereof. Means are provided for mounting the electrically resistive foil to the second surface of the plate.

Further, illustratively according to the invention, the instrument determines coagulation time by combining fluid blood, blood fraction or control with particles which are affected by a magnetic field so that the particles become suspended relatively freely in the fluid. The instrument further comprises means for generating a time-varying magnetic field for causing the particles to be reoriented as the magnetic field varies, with the reorientation changing as the fluid coagulates owing to the fluid's changing viscosity. Means are provided for mounting the means for generating the time-varying magnetic field adjacent the surface.

Illustratively, the cuvette comprises a region for bearing a code. The instrument further comprises one or more fifth radiation sources for irradiating the code bearing region, and one or more third detectors for detecting the transmission of radiation through the code bearing region. The fifth radiation source or sources and third detector or detectors are mounted adjacent the code bearing region to detect the code.

Further, illustratively, there are multiple fifth radiation sources and a single third detector. The third detector has an active region which extends adjacent the code bearing region to detect the transmission of radiation from all of said fifth radiation sources. Means are provided for activating the fifth radiation sources in a predetermined sequence to permit the detection and determination of the code borne by the code bearing region.

The invention may best be understood by referring to the following description and accompanying drawings which illustrate the invention. In the drawings:

FIG. 6 illustrates an enlarged exploded perspective view of a detail of FIG. 5;

Figure 1:
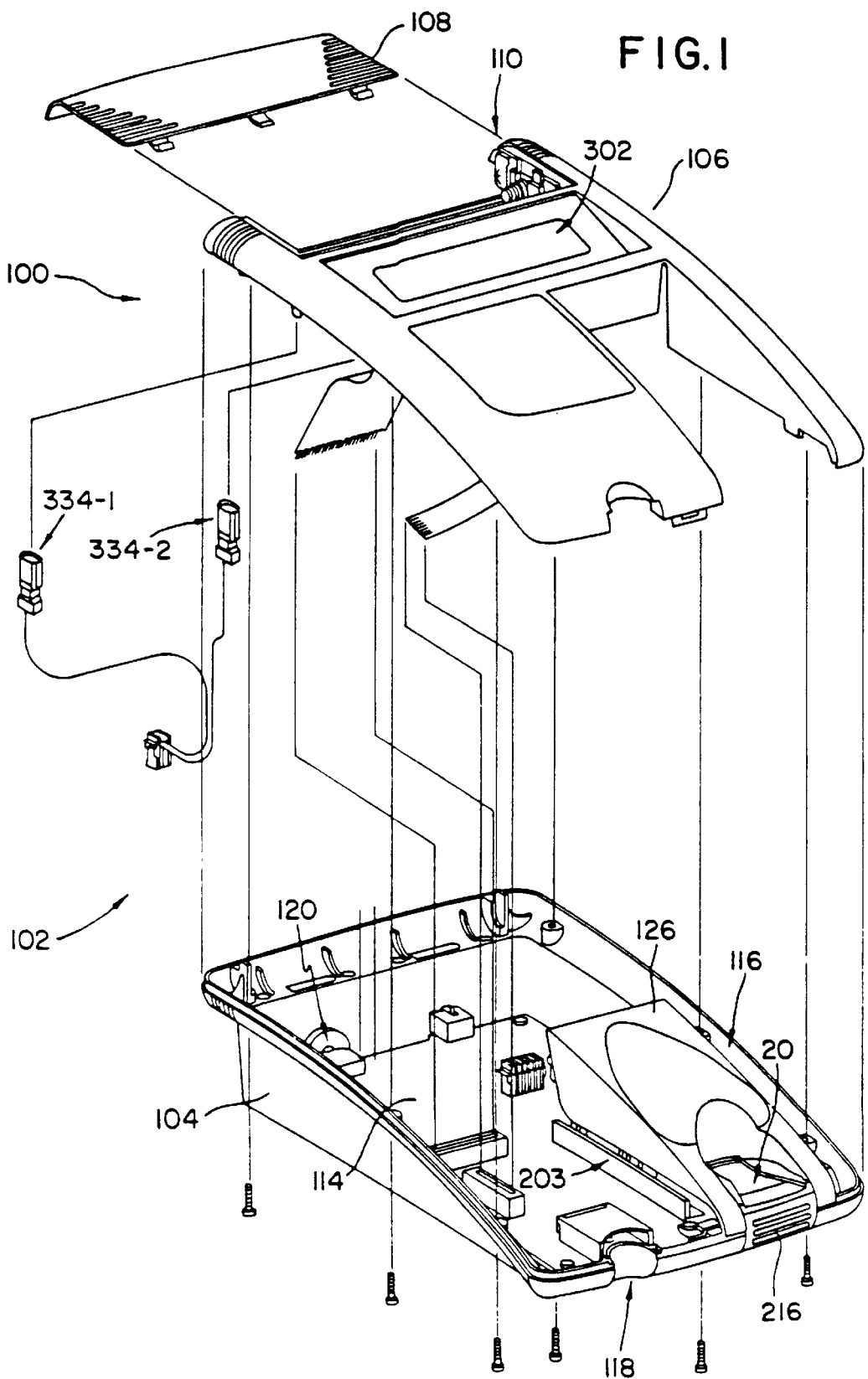
FIG. 1 illustrates an exploded perspective view of an instrument constructed according to the present invention.
Figure 2:
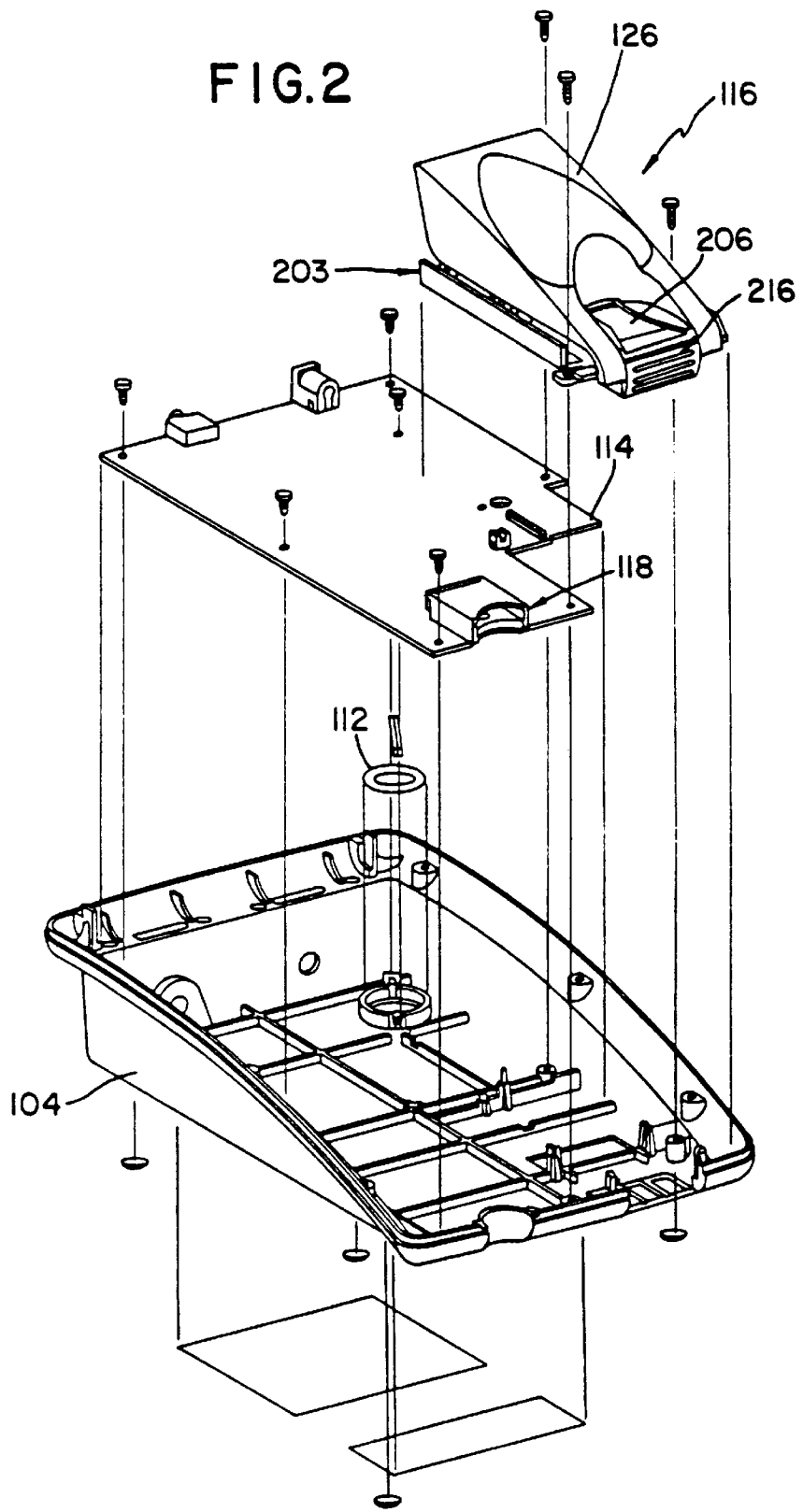
FIG. 2 illustrates a fragmentary exploded perspective view of the bottom portion of the instrument illustrated in FIG. 1.
Figure 3:
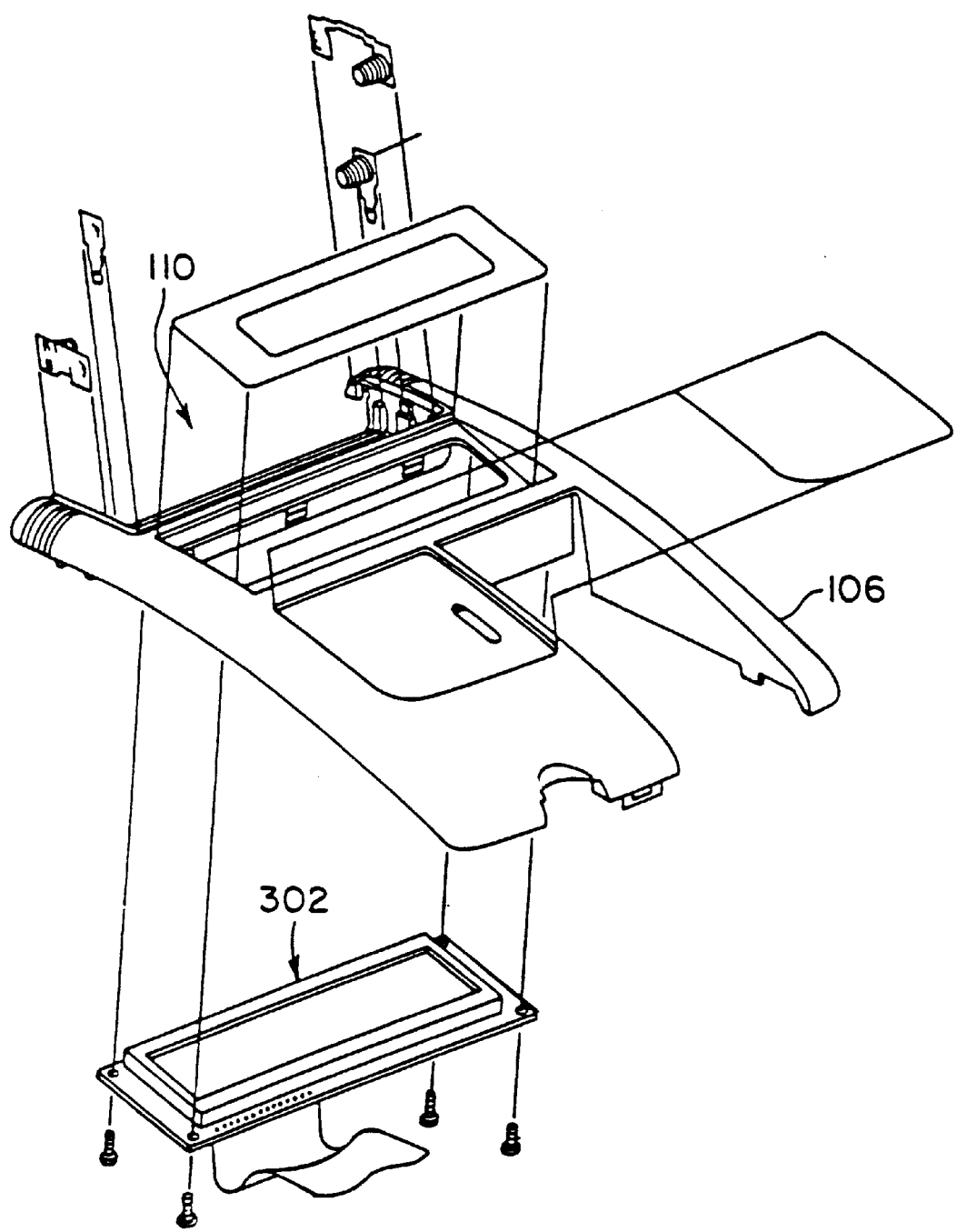
FIG. 3 illustrates a fragmentary exploded perspective view of the top portion of the instrument illustrated in FIG. 1.
Figure 4:
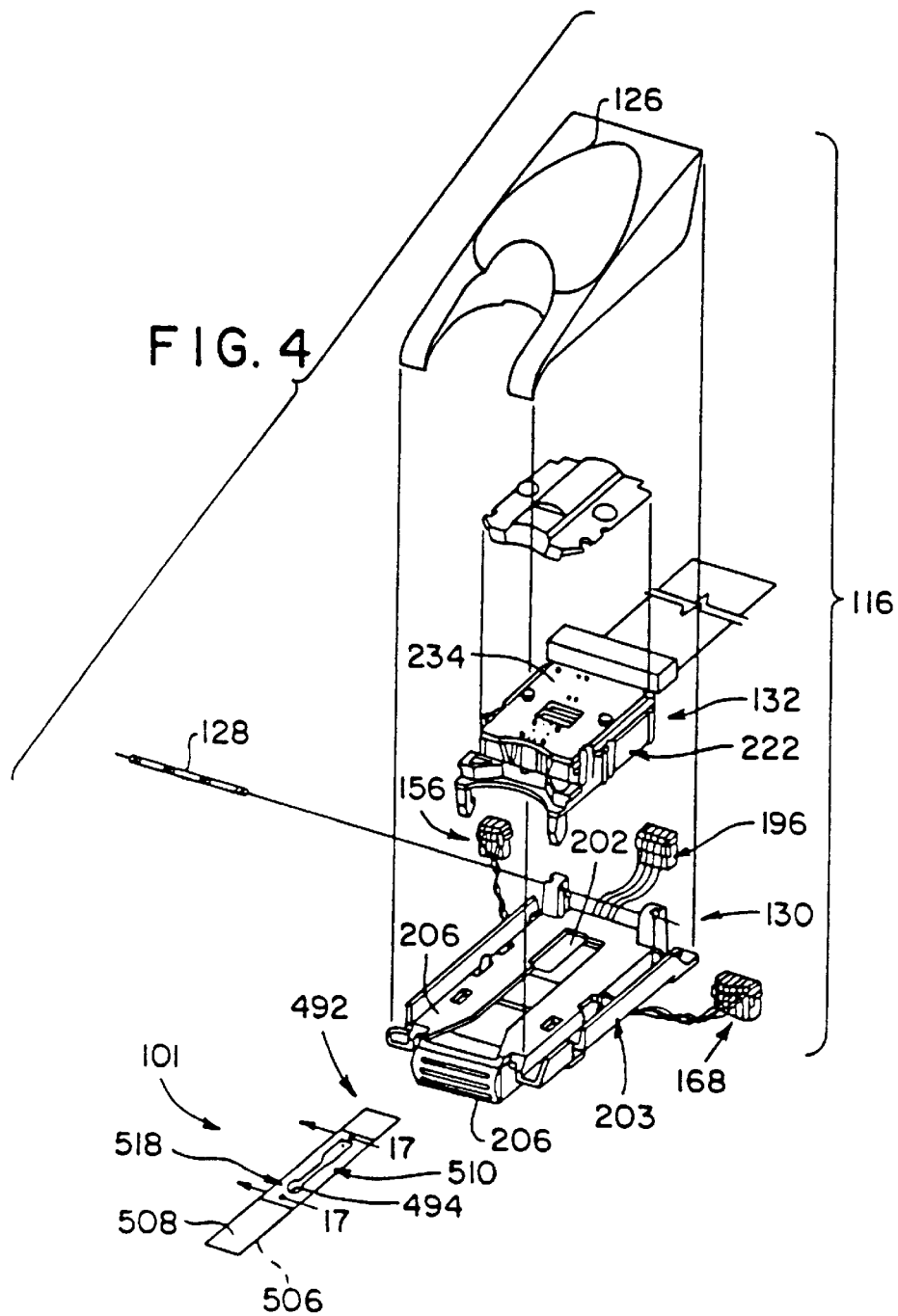
FIG. 4 illustrates an exploded perspective view of a detail of FIG. 1.
Figure 5:
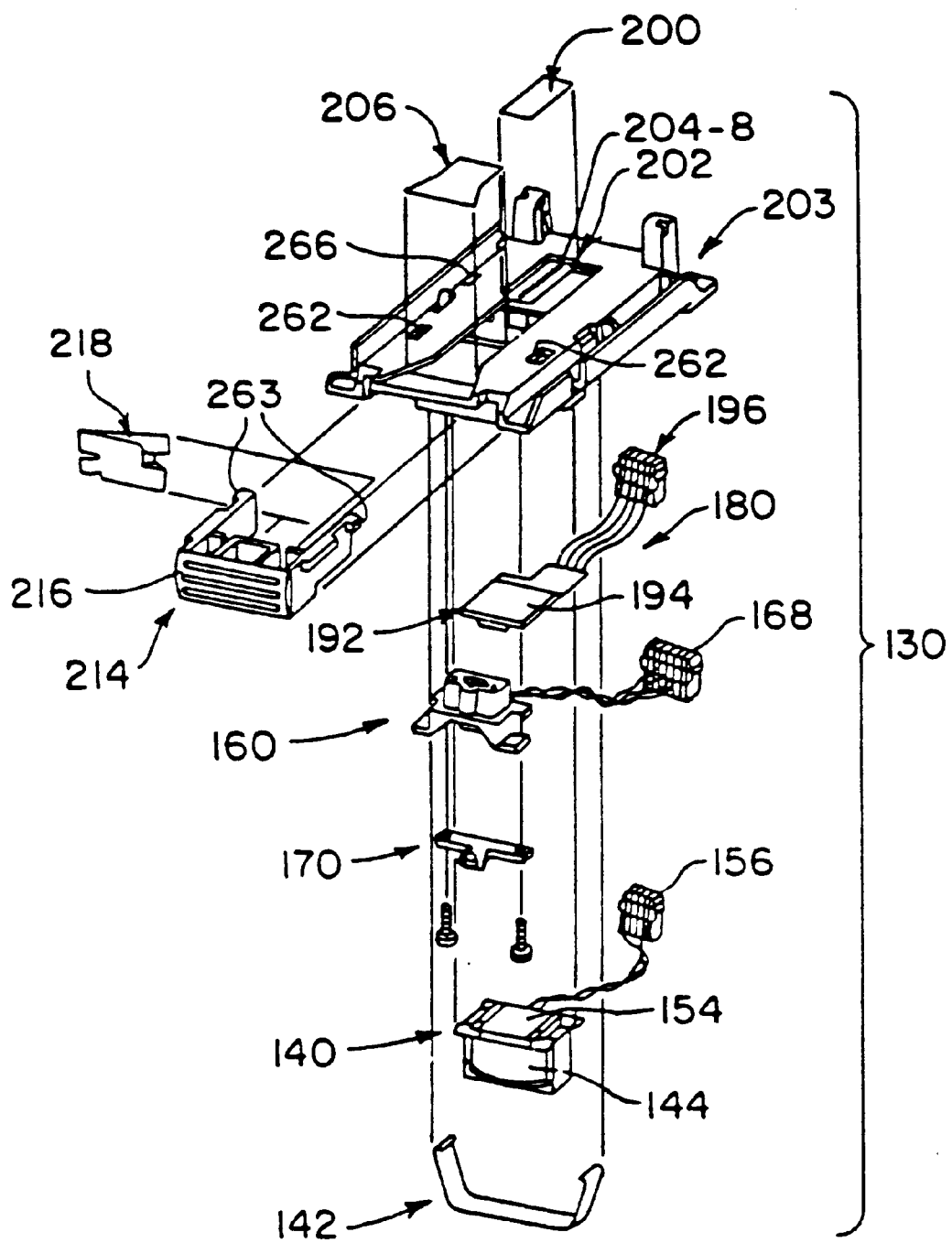
FIG. 5 illustrates an exploded perspective views of a detail of FIGS. 4.
Figure 7A:
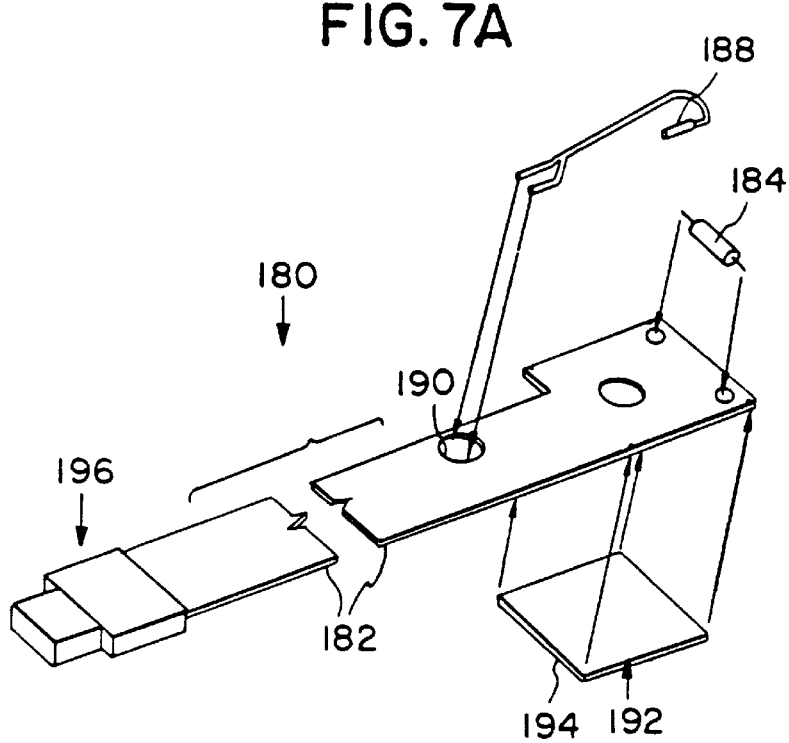
Figure 7B:
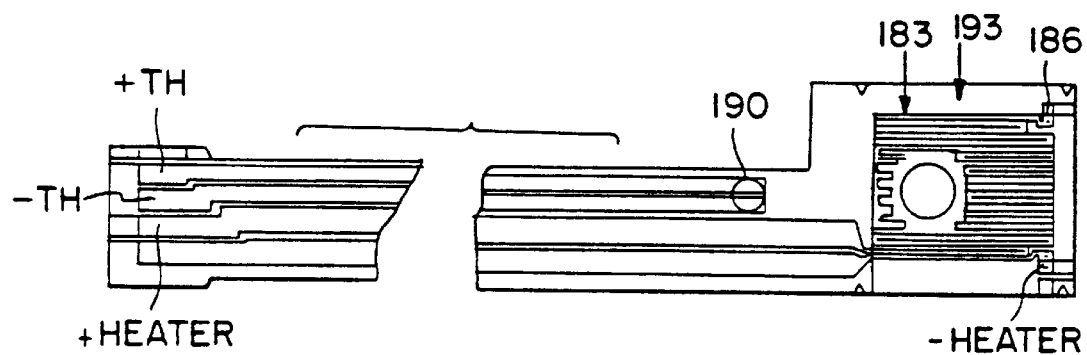
Figure 13:
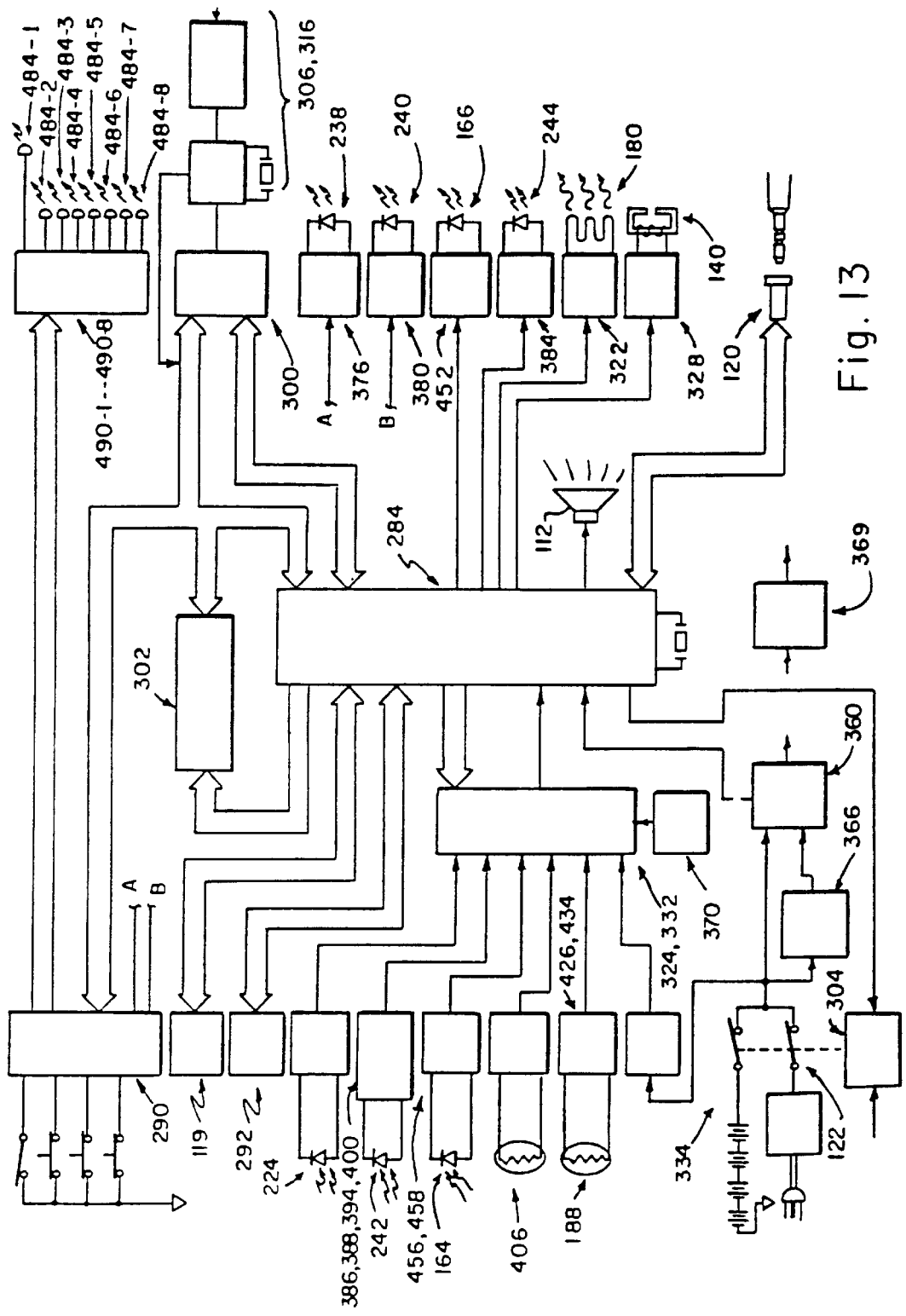
Figure 14:
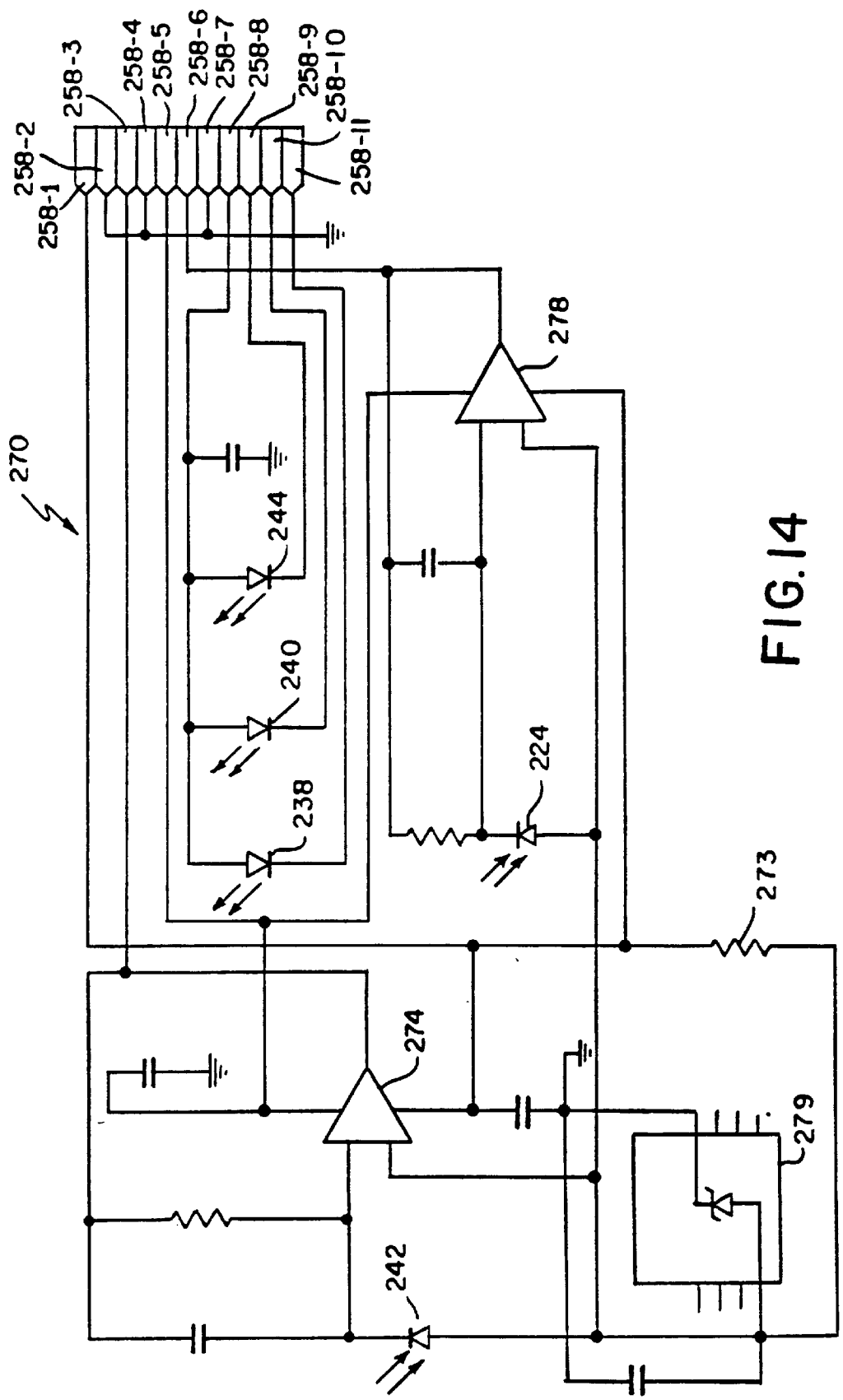
Figure 15A:
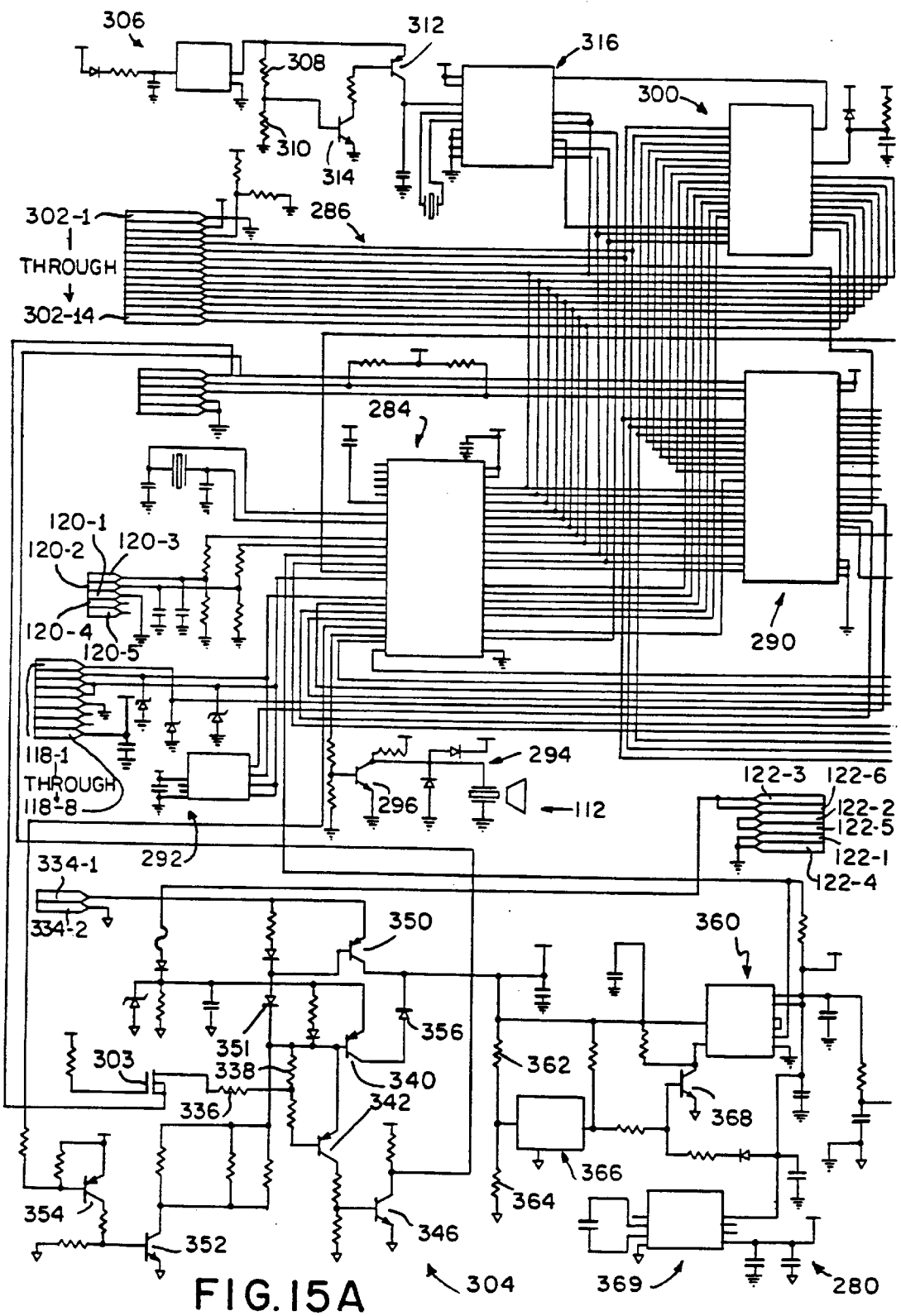
Figure 15B:
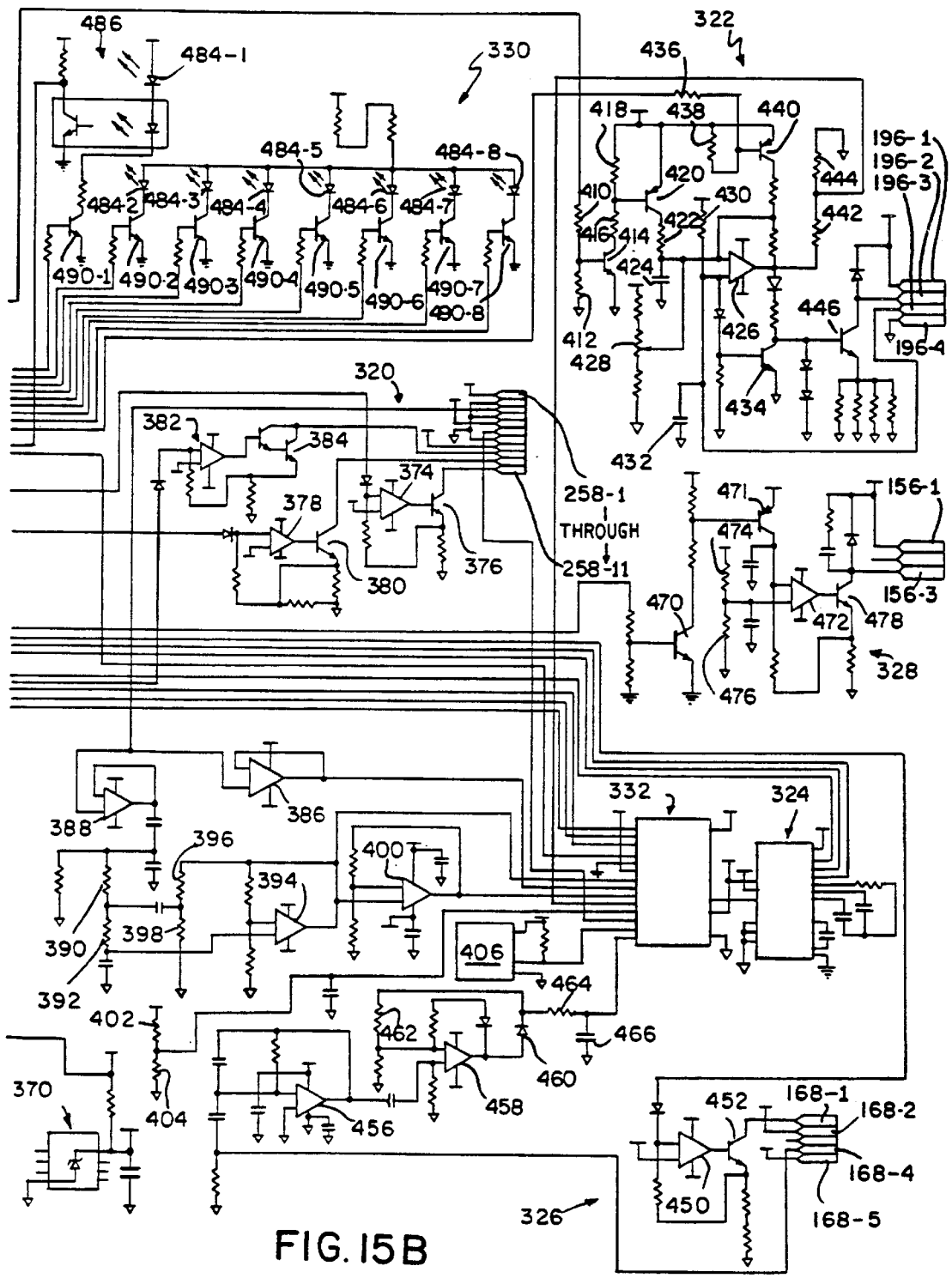
Figure 16:
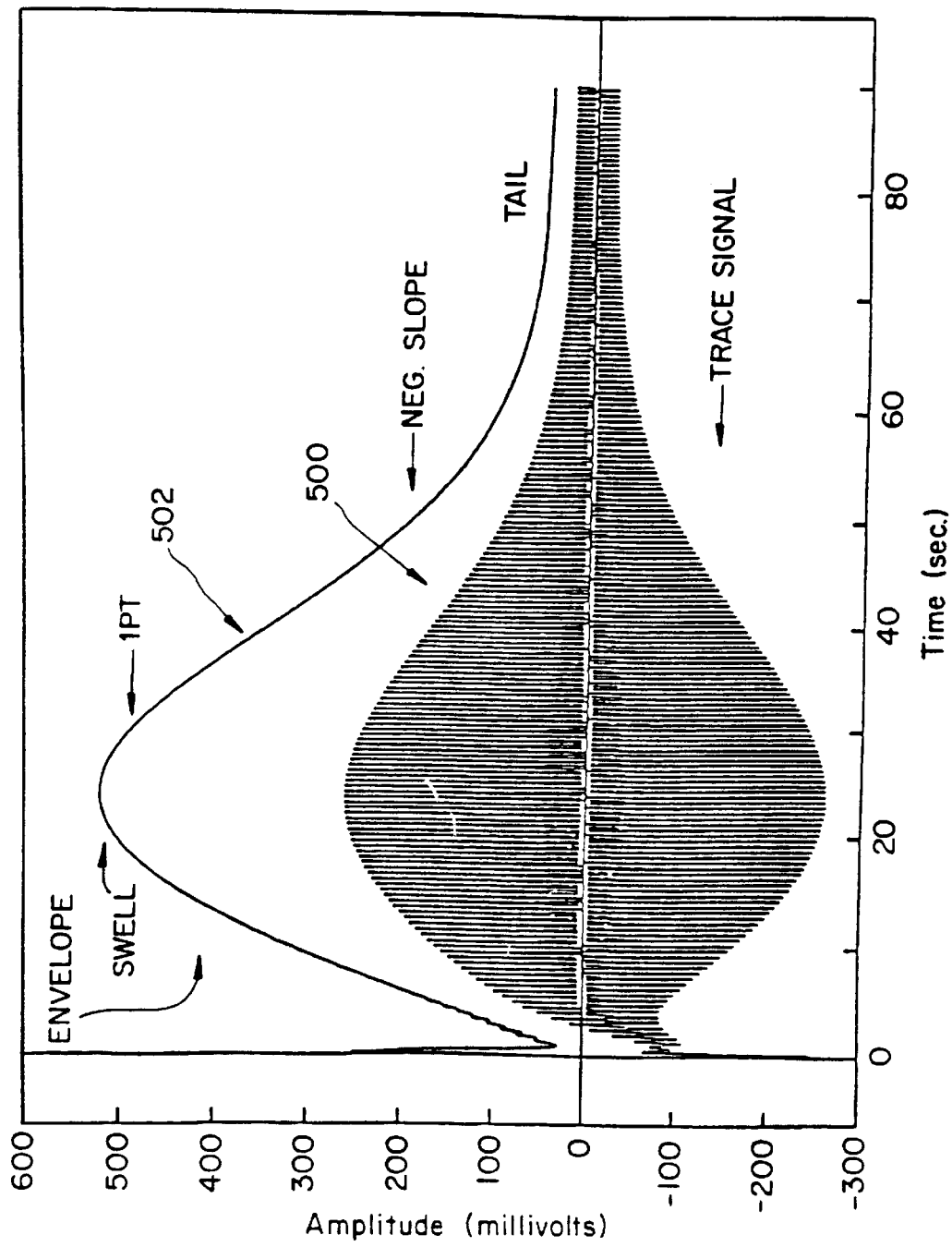
Figure 17A:
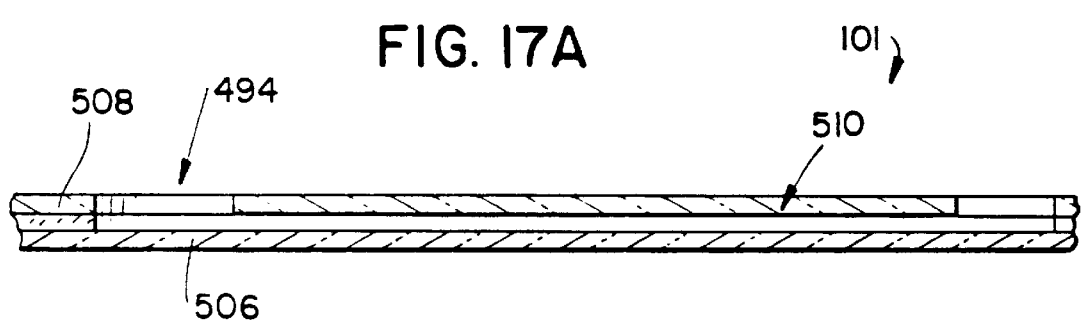
Figure 17B:
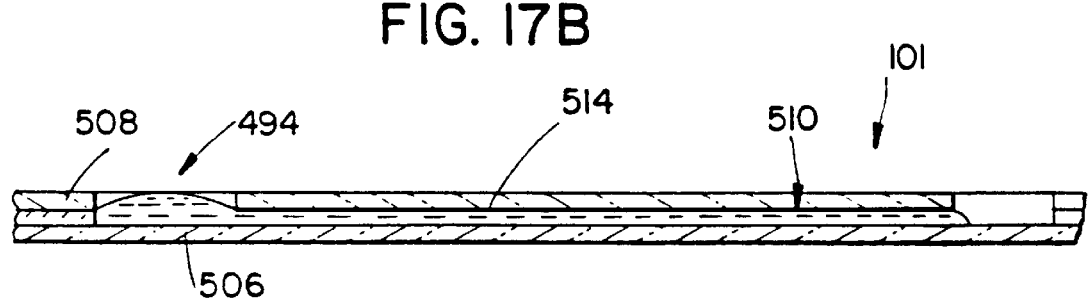
Figure 18:
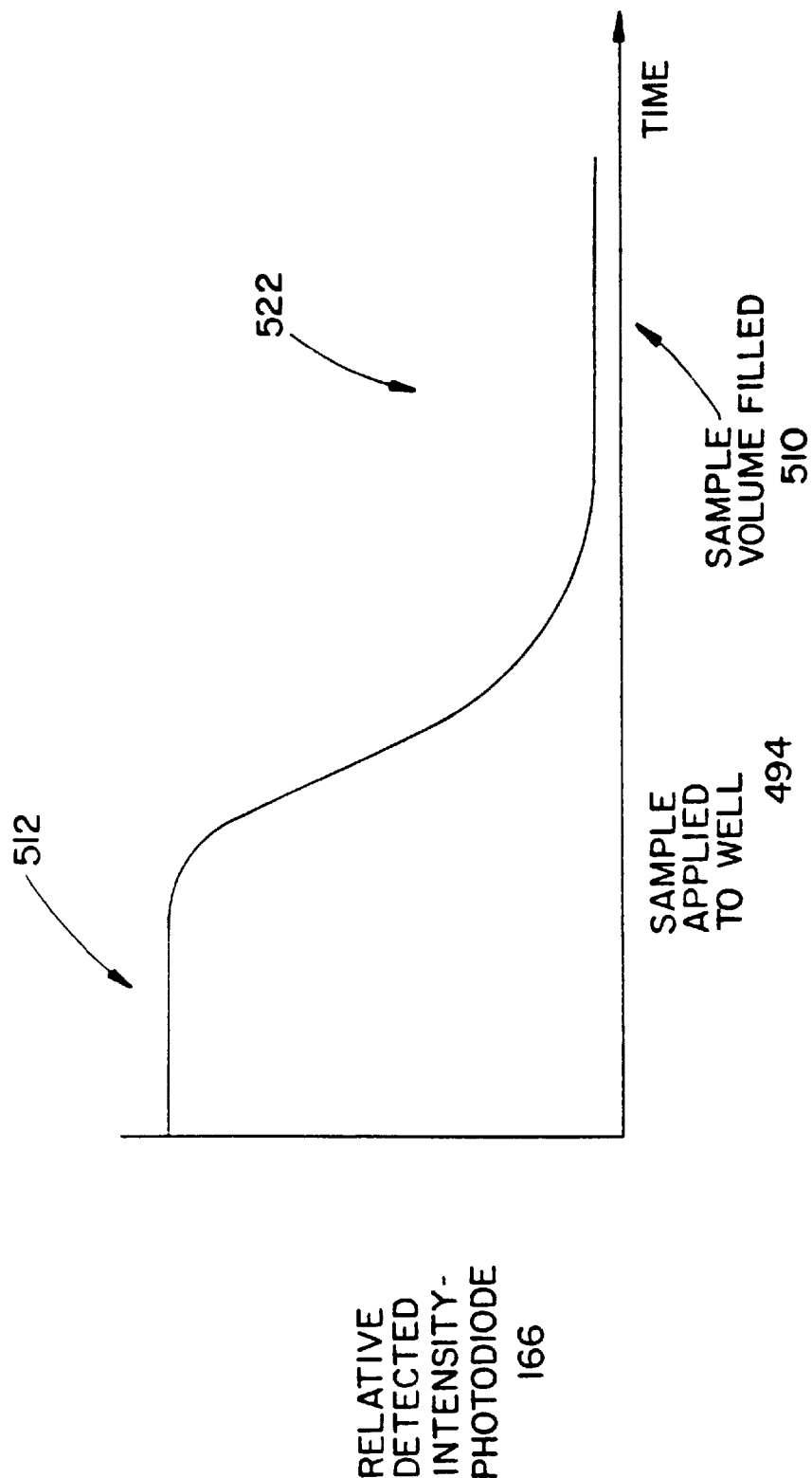

FIG. 7a–b illustrate an enlarged, fragmentary, exploded perspective view and a fragmentary bottom plan view, respectively, of a detail of FIG. 5;

FIGS. 8a–c illustrate a top perspective view, a different top perspective view, and a bottom perspective view, respectively, of a detail of FIG. 5;

FIGS. 9a–b illustrate an exploded bottom perspective view and an exploded top perspective view, respectively, of a detail of FIG. 5;

FIG. 10 illustrates a top plan view of a detail of FIG. 5;

FIGS. 11a–d illustrate exploded perspective views of details of FIG. 4;

FIGS. 12a–b illustrate perspective views from two different perspectives of a detail of FIG. 4;

FIG. 13 illustrates a block diagram of the electrical system of the instrument of FIG. 1;

FIG. 14 illustrates a schematic diagram of an electric circuit of the instrument of FIGS. 1 and 13;

FIGS. 15a–b illustrate a schematic diagram of an electric circuit of the instrument of FIGS. 1 and 13;

FIG. 16 illustrates a reflected light signal and a rectified reflected light envelope according to the present invention;

FIGS. 17a–b illustrate enlarged fragmentary longitudinal sectional views taken generally along section lines 17—17 of FIG. 4; and FIG. 18 illustrates a detected light profile according to the present invention.

The following schematic and block circuit diagram descriptions identify specific integrated circuits and other components and in many cases specific sources for these. Specific terminal and pin names and numbers are generally given in connection with these for the purposes of completeness. It is to be understood that these terminal and pin identifiers are provided for these specifically identified components. It is to be understood that this does not constitute a representation, nor should any such representation be inferred, that the specific components or sources are the only components available from the same or any other sources capable of performing the necessary functions. It is further to be understood that other suitable components available from the same or different sources may not use the same terminal/pin identifiers as those provided in this description.

An instrument 100 for determining the coagulation time of a specimen, whether of blood or of a control, includes a housing 102 comprising a housing bottom 104 and a housing top 106. Top 106 is provided with a battery door 108 which covers a battery well 110 housing the instrument 100's battery power source (not shown). Bottom 104 houses a Kyocera KBS26DA7A piezoelectric beeper 112, and a printed circuit board (PCB) 114 onto which are assembled various circuit components which will be described later. An optics assembly 116, a socket 118 for a test parameters electronically erasable programmable read-only memory (EEPROM) key 119 of the type described in U.S. Pat. No. 5,053,199, a socket 120 for serial data communication, and a power supply connector 122 for connection of instrument 100 to an external AC/DC adapter (not shown) for operation thereby in lieu of the batteries (not shown) with which instrument 100 is typically equipped, are also assembled onto PCB 114.

Optics assembly 116 includes a covered 126 strip adapter top assembly 132 hinged 128 to a strip adapter bottom assembly 130. Strip adapter bottom assembly 130 includes a magnet assembly 140 held to bottom assembly 130 by a spring clip retainer 142. Magnet assembly 140 includes an 850 turn (#32 A.W.G.) coil 144 wound on a bobbin 146 which is positioned over the center leg 148 of a 50% nickel/50% iron powdered metal E-core 150. The end legs 152 of E-core 150 lie outside coil 144. A nine-and-one-half pole per end, flat plate, barium ferrite bias magnet 154 is placed over the end of the center leg 148 and is supported on one end of the bobbin 146. A connector 156 permits electrical connections to be made to coil 144.

Strip adapter bottom assembly 130 also includes a sample port housing assembly 160 having a housing 162 within which are mounted a Siemens type BPW34F photodiode 164 and a Honeywell type SEP8705-003 LED 166. Photodiode 164 senses light generated by LED 166 and reflected from the sample and strip 101 to provide an indication that a sample, be it blood or control, has been applied to instrument 100 for testing. A connector 168 provides for electrical connections to photodiode 164 and LED 166. A clamp 170 retains LED 166 in housing 162. The angle between the axes of the LED 166 and photodiode 164 openings 172, 174, respectively, is about 15°.

Strip adapter bottom assembly 130 also includes a heater assembly 180 including a heater foil 182 constructed from two Kapton/WA polyamide films between which is sandwiched a copper nickel foil trace 183. A thermal fuse 184 and a thermistor 188 are mounted on the side of the foil 182 opposite the heater trace. Thermal fuse 184 is coupled through the foil 182 between one terminal 186 of the heater foil trace and the − HEATER terminal of a heater circuit. Contact is made to the leads of thermistor 188 from the THermistor + and − leads of the heater circuit through a hole 190 in the foil 182. An aluminum nitride heater plate 192 having a light reflecting top surface 194 is attached to foil 182 over the heater pattern area 193 of the heater trace using a thermosetting acrylic adhesive. Electrical connections are made to heater assembly 180 through a connector 196.

A transparent polycarbonate window 200 is adhesively attached to a region 202 of strip adapter bottom assembly housing 203 which is formed with a series of eight transversely extending slit openings 204-1–204-8, respectively. A transparent polycarbonate window 206 is provided with an opaque glossy black coating 208 over part of its surface and an opaque glossy yellow coating 210 over part of its surface. The remainder 211 of window 206 remains transparent. Remainder 211 overlies a slit 213 in housing 203 through which radiation from LED 166 is transmitted to the sample and through which remission from the sample is detected by photodiode 164. The yellow region 210 visible to the user of instrument 100 indicates where the sample, be it blood or control, is to be placed on a transparent disposable strip 101, such as those illustrated and described in U.S. Pat. No. 4,849,340 or the CoaguChek® coagulation system test strip available from Boehringer Mannheim Corporation, 9115 Hague Road, Indianapolis, Ind. 46250, when the disposable strip 101 is properly located in the optics assembly 116. A push-button latch 214 including a button 216 biased into locking position by a scissors-shaped compression spring 218 completes strip adapter bottom assembly 130.

Strip adapter top assembly 132 includes a strip adapter top 222 into which is mounted a Centronic type 4500094 bar code reading photodiode 224 with an elongated active region exposed through a slot 226 and a transparent polycarbonate window 228 adhesively mounted on the underside of top 222 to close slot 226. A photosensor bracket 230 captures photodiode 224 in position adjacent slot 226. Test strip clamps containing foam springs 232, useful in pressing test strip 101 against heater plate 192, have tabs that fit into locating openings provided therefor in the floor of top 222. Space 235 is provided between clamps 232 to accommodate a positioning bracket 236 which is mounted on the underside of PCB 234 and extends downward therefrom into space 235. Siemens type SFH405-3 START LED 238 and FILL LED 240 are mounted respectively in front of and behind positioning bracket 236 angled at about 50° to the normal plane of incidence on PCB 234. A Siemens type BPW34F photodiode 242 with a daylight filter is mounted on PCB 234 inside positioning bracket 236. All three of components 238, 240, 242 are exposed downward through openings provided therefor in the bottom of strip adapter top 222 of the strip adapter top assembly 132. An Optek type OP290A MAIN assay LED 244 is mounted in an opening 246 provided therefor in strip adapter top 222 and is held in place by a holding clamp 248. The leads of LED 244 are connected to PCB 234. The axis of opening 246 makes an angle of about 45° with the axis of the opening for photodiode 242 and intersects it.

A pop-up bracket 250 is spring 252-loaded into an opening provided therefor in a rear end wall 254 of strip adapter top 222 to cause the strip adapter top assembly 132 to pop up when button 216 is pushed. An eleven-conductor flat cable 256 and connector 258 make the connections between the components mounted on PCB 234 and the remaining circuits of the PCB 114. Pawl-type catches 260 extend downward from the two forward corners of strip adapter top 222. Openings 262 are provided adjacent the front corners of strip adapter bottom assembly 130 to accommodate catches 260. Cooperating tongues 263 on button 216 are urged into engagement with catches 260 by spring 218 when strip adapter bottom assembly 130 and top assembly 132 are closed together. A flag 264 which extends downward from a side edge of strip adapter top 222 extends into a slot 266 provided for this purpose in strip adapter bottom assembly 130 where flag 264 interrupts a light path from a source to a detector to indicate that the strip adapter top and bottom assemblies 132, 130, respectively, are closed together.

The electrical circuitry on PCB 114 powers and reads the various sensors included on the coagulation optics circuit 270 on PCB 234. +5 V and −5 V are supplied to circuit 270 through terminals 258-5 and 258-1, respectively, of connector 258. Unregulated voltage is supplied to terminal 258-8 of connector 258. Ground for circuit 270 is provided at terminals 258-2, 4 and 7 of connector 258. A 1 μF, 25 V capacitor is coupled across terminals 258-8 and 258-2, 4, 7. The anodes of LEDs 238, 240, 244 are all coupled to terminal 258-8. The cathode of LED 238 is coupled to the START terminal, terminal 258-11, of connector 258. The cathode of LED 240 is coupled to the FILL terminal, terminal 258-10, of connector 258. The cathode of LED 244 is coupled to the MAIN terminal, terminal 258-9, of connector 258.

The anodes of photodiodes 224, 242 are coupled through a 100 KΩ resistor 273 to terminal 258-1. The cathode of photodiode 242 is coupled to the − input terminal of an operational amplifier 274. The + input terminal of operational amplifier 274 is coupled to the anodes of photodiodes 224, 242. The output terminal of operational amplifier 274 is coupled to its − input terminal through a parallel RC feedback circuit including a 560 pF capacitor and a 2.21 MΩ, 1%, 50 parts-per-million thermal coefficient resistor. The output terminal of operational amplifier 274 is also coupled to the DETect terminal, terminal 258-3, of connector 258.

The cathode of photodiode 224 is coupled to the − input terminal of an operational amplifier 278. The + input terminal of operational amplifier 278 is coupled to the anodes of photodiodes 224, 242. The output terminal of operational amplifier 278 is coupled to its − input terminal through a parallel RC feedback circuit including a 0.001 μF capacitor and a 499 KΩ, 1% resistor. The output terminal of differential amplifier 278 is also coupled to the CodeBaR OUTput terminal, terminal 258-6, of connector 258. Operational amplifiers 274, 278 illustratively are National Semiconductor type LPC662IM operational amplifiers.

A +V terminal of a National Semiconductor type LM385M-2.5, 2.5 V reference voltage source 279 is coupled to terminals 258-2, -4 and -7 of connector 258. The − terminal of reference voltage source 279 is coupled to the anodes of photodiodes 224, 242, to the + input terminals of operational amplifiers 274, 278, and through resistor 273 to the −5 V terminal, 258-1, of connector 258.

The electric circuitry 280 mounted on PCB 114 processes the various signals from circuitry 270, as well as others which circuitry 280 generates itself or receives from the user of instrument 100, or which are generated externally to instrument 100. An Intel type N83C51FC eight-bit microcontroller (μC) 284 has data terminals P0.0–P0.7 coupled to DATA lines 0–7, respectively, of an instrument 100 bus 286. μC 284 address terminals P2.0–P2.4 and P2.6–P2.7 are coupled to address lines A8–A12 and A14–A15, respectively, of bus 286. The ReaD and WRite terminals, P3.7 and P3.6, respectively, of μC 284, are coupled to the Read Data and Write Data lines, respectively, of bus 286. An Address Latch Enable terminal of μC 284 is coupled to the ALE terminal of a Toshiba type TC11L003AU-1031 application specific programmable gate array integrated circuit (ASIC) 290. The TIP (transmit) terminal 120-2 of serial data port socket 120 is coupled through the parallel combination of a 120 pF capacitor and a 220 KΩ resistor to ground, and through a 10 KΩ series resistor to the Transmit Data (TXD) terminal P3.1 of μC 284. The RING (receive) terminal 120-3 of serial data port socket 120 is coupled through the parallel combination of a 120 pF capacitor and a 220 KΩ resistor to ground and through a 1.2 KΩ series resistor to the Receive Data (RXD) terminal P3.0 of μC 284. The GrouND terminal 120-1 of socket 120 is coupled to ground.

The CS terminal 118-1 of ROM key socket 118 is coupled through a Philips type BZV55C6V2 6.2 V Zener diode to ground and directly to a Code ROM IC chip Select OutPut terminal 22 of ASIC 290. The SK terminal, 118-2, of ROM key socket 118 is coupled through a type BZV55C6V2 Zener diode to ground and directly to the CLOCK terminal, terminal P1.0, of μC 284. It is also coupled to the SK terminal of a Samsung type 93C46AK EEPROM 292 internal to instrument 100. EEPROM 292 generally contains the meter 100 characterizing parameters. The DI and DO terminals, terminals 118-3 and 4, of socket 118 are coupled to each other, to ground through a BZV55C6V2 Zener diode, directly to the DI and DO terminals of EEPROM 292, and directly to the EEDI/DO terminal P3.5, of μC 284. Terminal 118-5 of socket 118 is coupled to ground. Terminal 118-8 of socket 118 is coupled to the system +5 V supply.

The time base for μC 284 is generated by a 7.3728 MHz crystal which is coupled across terminals X1-X2 thereof. A 27 pF capacitor is coupled between each terminal of the crystal and ground. Terminal P1.5 of μC 284 is coupled to a resistive voltage divider including two series 100 KΩ resistors in a beeper 112 driver circuit 294. The common terminal of the series 100 KΩ resistors is coupled to the base of a Siemens type BC848C driver transistor 296. The collector of transistor 296 is coupled through a 1 KΩ pull-up resistor to +5 V and directly to one terminal of beeper 112. The emitter of transistor 296 and the other terminal of beeper 112 are both coupled to ground. Two type LL4148 diodes clamp the collector of transistor 296 between ground and +5 V.

The data terminals D0–D7 of a Samsung type LH5164-10 8 K by 8 static random access memory (SRAM) 300 are coupled to the DATA 0–DATA 7 lines, respectively, of bus 286. The address terminals A0–A12 of SRAM 300 are coupled via the system bus 286 to the A0–A7 terminals of ASIC 290 and the A8–A12 terminals of μC 284, respectively. The ReaD and WRite terminals of SRAM 300 are coupled via the bus 286 to the ReaD and WRite terminals, respectively, of μC 284. The CE2 terminal of SRAM 300 is coupled to the junction of a 390 KΩ resistor and a 0.1 pF capacitor. The other terminal of the resistor is coupled to +5 V. The other terminal of the capacitor is coupled to ground. The CE2 terminal is clamped via a type LL4148 diode to +5 V. The DATA 0–DATA 7 terminals of a Samtron type UC16203GNAR two line by sixteen character display 302 are coupled to the DATA 0–DATA 7 terminals of bus 286. The DISPlay ENable terminal of display 302 is coupled via bus 286 to the DISPlay ENable terminal of ASIC 290. The A0–A1 terminals of display 302 are coupled to the A0–A1 terminals, respectively, of bus 286. The GrouND terminal of display 302 is coupled to the system ground and the VDD terminal of display 302 is coupled to +5 V. Terminal 3 of display 302 is coupled through a 1 KΩ resistor to ground and through an 18 KΩ resistor to +5 V. An instrument 100 keypad switch has its ON/OFF terminal connected to the source of a Samsung type BSS139 field effect transistor (FET) 303 in instrument 100's power supply circuit 304. The YES terminal of the switch is coupled to InPut terminal 1 of ASIC 290. The NO terminal of the switch is coupled to InPut terminal 2 of ASIC 290. The YES and NO terminals are also coupled through respective 1 MΩ pull-up resistors to +5 V.

Battery back-up protection is provided to SRAM 300 by a circuit including a 3.3 V regulator 306. The $V_{in}$ terminal of regulator 306 is coupled to the junction of a resistor and a capacitor. The other terminal of the capacitor is coupled to ground. The other terminal of the resistor is coupled to the cathode of a diode, the anode of which is coupled to +VBAT. The $V_{out}$ terminal of regulator 306 is coupled across a series resistive voltage divider including a resistor 308 and a resistor 310 to ground. $V_{out}$ is also coupled to the emitter of a transistor 312. The junction of resistors 308, 310 is coupled to the base of a transistor 314. The emitter of transistor 314 is coupled to ground. Its collector is coupled through a series resistor to the base of transistor 312. The collector of transistor 312 is coupled to the BATtery 1 terminal of a real time clock 316, and to one terminal of a capacitor, the other terminal of which is coupled to ground. The D and Q terminals of IC 316 are coupled to the DATA 0 line of bus 286. The $\overline{\text{CEI}}$, $\overline{\text{CEO}}$, $\overline{\text{WE}}$ and $\overline{\text{OE}}$ terminals of IC 316 are coupled to terminal P2.7(A15) of μC 284, terminal $\overline{\text{CE}}$ of SRAM 300, the Write Dataline of bus 286, and the Read Data line of bus 286, respectively. The VCC OUTPUT terminal of IC 316 is coupled to the VDD terminal of SRAM 300 and through a capacitor to ground. The time base for IC 316 is generated by a crystal coupled across terminals X1-X2 thereof.

The PoWeR INTerrupt, MAIN ConTroL, HeaTeR ON/OFF, A/D OUT, A/D A, A/D B, power SUPPLY ON, SAMPLE ConTroL, and MAGnet 1 ConTroL terminals, terminals P3.2, P3.3, P3.4, P1.1, P1.2, P1.3, P1.4, P1.6 and P1.7, respectively of μC 284, are coupled to the power supply circuit 304, the main LED driver in an LED driver circuit 320, the heater control circuit 322, the COMParator OUTput terminal of a Teledyne type TSC500ACOE A/D converter IC 324 in the analog section of instrument 100, the A terminal of A/D 324, the B terminal of A/D 324, power supply circuit 304, the sample port circuit 326, and the magnet current control circuit 328.

The InPut 3 terminal of ASIC 290 is coupled to an Omron type EE-SX 1067 optical switch 486. The OutPut 10–17 terminals of ASIC 290 are coupled to the bar code LED array driver circuit 330. The OutPut terminals 20, 21, 24 and 25 of ASIC 290 are coupled to the setpoint temperature control of heater driver circuit 322, the LATCH ENABLE terminal of a Signetics type 74HC4351DW eight-to-one analog multiplexer 332 in the analog section of instrument 100, the fill LED driver in circuit 320, and the start LED driver in circuit 320, respectively. The Address 0–2 lines of bus 286 are coupled to the A, B and C terminals, respectively, of multiplexer 332.

Power supply circuit 304 includes an instrument 100 battery connector 334 having +VBAT terminal 334-1 and ground terminal connector 334-2 and AC/DC converter power supply connector 122 having +VIN terminals 122-3 and 6 connected together and GRouNd terminals 122-1 and 4 connected together. +VBAT is coupled through a series resistor to the gate of FET 303. The drain of FET 303 is coupled through two series resistors 336, 338 to the base of a transistor 340. The emitter of transistor 340 is coupled to its base through the series combination of a resistor and a diode, through a diode and 2.0 ampere fuse to +VIN, and through a parallel combination of a transient suppressor diode, a resistor and a capacitor to ground. The junction of resistors 336, 338 is coupled through a resistor to the base of a transistor 342. The emitter of transistor 342 is coupled to the base of transistor 340. The collector of transistor 342 is coupled through two series resistors to ground. The common terminal of these resistors is coupled to the base of a transistor 346. The emitter of transistor 346 is coupled to ground and its collector is coupled through a pull-up resistor to +5 V. The collector of transistor 346 is also coupled to InPut terminal 0 of ASIC 290.

The emitter of a transistor 350 is coupled to +VBAT. +VBAT is coupled through a resistor and a diode in series to the base of transistor 350. The base of transistor 350 is coupled through a diode 351 to the base of transistor 340. The base of transistor 340 is coupled through a parallel resistance network to the collector of a transistor 352. The emitter of transistor 352 is coupled to ground. Its base is coupled through a resistor to ground and through a resistor to the collector of a transistor 354. The emitter of transistor 354 is coupled to +5 V Analog. The base of transistor 354 is coupled through a resistor to +5 VA. The base of transistor 354 is also coupled through a resistor to terminal P1.4 of μC 284. Once the on/off key to meter 100 is depressed upon turn-on, enough time is given for the +5 V supply to come up and the μC 284 to reset itself (once +5 V supply has been applied to its $V_{cc}$ pin) and then to have terminal P1.4 of μC 284 latch the system +5 V supply on. This terminal is also used to shut the system down in an orderly fashion. VUN-REGulated appears at the collector of transistor 350 and at the cathode of a diode 356, the anode of which is coupled to the collector of transistor 340.

Regulation is initiated by battery voltage +VBAT on the gate of FET 303. If the battery is in backward, or is below minimum regulation level and no AC/DC adapter is connected to instrument 100, or is missing and no AC/DC adapter is connected to instrument 100, the instrument 100 cannot be turned on. If the battery is installed properly and is above minimum regulation level, regulation is established at the base of transistor 340 and, through diode 351, at the base of transistor 350. Regulation is also signalled through transistors 342 and 346 to the ON/OFF INDicator InPut terminal 0 of ASIC 290. If the battery voltage +VBAT is greater than +VIN, diode 356 decouples the AC/DC adapter input circuitry, including transistor 340 and its associated regulating circuitry from VUNREGulated so that the battery does not power that circuitry.

VUNREGulated is supplied to the VIN terminal of a +5 V regulator IC 360. VUNREGulated is also supplied to a series voltage divider including a resistor 362 and a resistor 364. The common terminal of resistors 362, 364 is coupled to the INput terminal of a voltage detector IC 366. The ERROR output terminal of IC 366 is coupled through a resistor to VUNREGulated and through a resistor to the base of a transistor 368. The collector of transistor 368 is coupled through a load resistor to VUNREGulated and is coupled directly to the SHUTDOWN terminal of +5 V regulator IC 360. If the supply voltage is low, IC 366 will prevent instrument 100 from being turned on. Regulated +5 V for the digital circuitry of instrument 100 appears at the VOUT terminal of +5 V regulator IC 360. The SENSE terminal of IC 360 is coupled to +5 V. The ERROR terminal of IC 360 is coupled through a pull up resistor to +5 V. The ERROR terminal is also coupled to the PoWeRINTerrupt terminal, P3.2, of μC 284. The error terminal's main function is to warn the μC 284 that the system power is approaching an unregulated condition. By warning μC 284 of such condition, μC 284 can power down the system in an orderly fashion prior to any soft failures occurring. A capacitor across VOUT and GrouND of IC 360 is decoupled by a resistor from a tantalum capacitor across the +5 VAnalog supply to analog ground. The voltage across the VOUT output terminal to ground is fed back through a diode and resistor in series to the base of transistor 368. The VOUT output terminal of IC 360 is also coupled to the V+ terminal of a +5 V-to--5 V converter 369. A tantalum capacitor is coupled across the CAP+ and CAP-terminals of converter 369. -5 VDC for circuits requiring it appears across the VOUT terminal of converter 369 to ground. The instrument 100's analog and digital grounds are tied together here. A +V terminal of a 2.5 V reference voltage source 370 is coupled through a resistor to +5 VAnalog. 2.5 VREFerence is established across the +V terminal of source 370 and ground.

Turning now to the LED driver circuitry 320 for the optical head assembly 116, the start LED control OutPut terminal 25 of ASIC 290 is coupled through a type LL4148 diode to the − input terminal of a Samsung type LM324A operational amplifier 374. The + input terminal of operational amplifier 374 is coupled to VREF. The output terminal of operational amplifier 374 is coupled to the base of a Philips type PXT4401 transistor 376. The collector of transistor 376 is coupled to the START LED terminal, terminal 258-11, of connector 258. The emitter of transistor 376 is coupled to ground through a 100 Ω resistor, which limits the current through the start LED at a constant current, and through a 100 KΩ feedback resistor to the − input terminal of operational amplifier 374.

The FILLConTroL terminal, OutPut terminal 24, of ASIC 290 is coupled through a type LL4148 diode to the − input terminal of a type LM324A operational amplifier 378. The + input terminal of operational amplifier 378 is coupled to VREF. The output terminal of operational amplifier 378 is coupled to the base of a type PXT4401 NPN transistor 380, the collector of which is coupled to the FILL LED terminal, terminal 258-10, of connector 258. The emitter of transistor 380 is coupled through a parallel resistor network, the effective resistance of which is 50 Ω, to ground, which limits the current through the fill LED at a constant current, and through a 100 KΩ feedback resistor to the − input terminal of operational amplifier 378.

The MAIN ConTroL terminal, P3.3, of μC 284 is coupled through a type LL4148 diode to the − input terminal of a type IM324A operational amplifier 382. The + input terminal of operational amplifier 382 is coupled to VREF. The output terminal of operational amplifier 382 is coupled to the base of a Philips type PXTA14 Darlington-coupled transistor pair 384. The collectors of transistors 384 are coupled to the MAIN assay LED terminal, 258-9, of connector 258. The emitter of transistors 384 is coupled through a 100 Ω 1%, 25 parts-per-million temperature coefficient resistor to ground, which limits the current through the main LED at a constant current, and through a 100 KΩ resistor, to the − input terminal of operational amplifier 382.

The sensed bar code of the disposable test strip 101 which is being used in a particular test comes in to circuit 320 serially on the CodeBaR terminal, 258-6, of connector 258. It is coupled directly to analog input terminal X5 of multiplexer 332. The START, FILL and MAIN assay DETect signals indicating that an adequate volume sample droplet has been placed over yellow area 210 on a test strip 101, and its raw coagulation results data, are provided from terminal 258-3 of connector 258 to the + input terminals of two type LM324A operational amplifiers 386, 388. Operational amplifier 386 is configured as a unity gain buffer and its output terminal is coupled to the DC input terminal X1 of multiplexer 332. Operational amplifier 388 is also configured as a unity gain buffer and its output terminal is capacitively coupled through a 0.1 μF capacitor and two series 100 KΩ resistors 390, 392 to a + input terminal of a type LPC662IM operational amplifier 394. The output terminal of operational amplifier 388 is also coupled to ground through an RC parallel combination of a 1.5 MΩ resistor and 0.0033 μF capacitor. The + terminal of operational amplifier 394 is coupled to ground through a 0.056 μF capacitor. The output terminal of operational amplifier 394 is coupled through a 2 MΩ, 1% feedback resistor to its − input terminal. Its − input terminal is coupled to ground through a 221 KΩ, 1% resistor. The output terminal of operational amplifier 394 is also coupled through series 100 KΩ, 1% and 20 KΩ, 1% resistors 396, 398, respectively, to ground. The common terminal of resistors 396, 398 is coupled through a 0.056 μF capacitor to the common terminal of resistors 390, 392.

The signal at the output terminal of operational amplifier 394 is directly coupled to the X0 input terminal, AC1, of multiplexer 332. That signal is also coupled to the + input terminal of a type LPC662IM operational amplifier 400. The signal at the output terminal of operational amplifier 400 is directly coupled to the X2 input terminal, AC2, of multiplexer 332. The output terminal of operational amplifier 400 is also coupled through a 3 MΩ, 5% resistor to the − input terminal thereof. The − input terminal of operational amplifier 400 is coupled through a 1 MΩ, 5% resistor to ground.

VUNREGulated is coupled through a series voltage divider including a resistor 402 and a resistor 404 to ground. The common terminal of resistors 402, 404 is coupled directly to the analog BATTery voltage input terminal X4 of multiplexer 332. +5 VA is coupled to the VDD input terminal of a temperature sensor 406. The VOUT terminal of sensor 406 is coupled directly to the analog VTEMP voltage input terminal, X6, of multiplexer 332 and through a pull-up resistor to +5 VA.

The heater control circuit 322 includes two series resistors 410, 412 coupled between the HeaTeR ON/OFF terminal of μC 284 and ground. The common terminal of resistors 410, 412 is coupled to the base of a transistor 414, the collector of which is coupled through two series resistors 416, 418 to +5 VA, and the emitter of which is coupled to ground. The common terminal of resistors 416, 418 is coupled to the base of a transistor 420, the emitter of which is coupled to +5 VA, and the collector of which is coupled through a series resistor 422 and capacitor 424 to ground. The common terminal of resistor 422 and capacitor 424 is coupled to the − input terminal of an operational amplifier 426.

+5 VA is coupled through a series resistor, a potentiometer 428 and a resistor to ground. The movable contact of potentiometer 428 is coupled to the − input terminal of operational amplifier 426. The potentiometer enables the heater plate 192 to achieve about 39° C. +5 VA is coupled through a series resistor 430 and capacitor 432 to ground. The common terminal of resistor 430 and capacitor 432 is coupled to the THermistor + terminal, 196-3, of connector 196, and to the + input terminal of operational amplifier 426. The + input terminal of operational amplifier 426 is coupled through the series combination of a diode and a resistor to ground. The junction of the resistor and diode is coupled to the base of a transistor 434, the emitter of which is coupled to ground. The output terminal of operational amplifier 426 is coupled through a resistor to its − input terminal and through the series combination of a diode and a resistor to the collector of transistor 434.

The SETPoinT 2 terminal, OutPut terminal 20, of ASIC 290, is coupled through series resistors 436, 438 to +5 VA. The ASIC 290 provides control of the heater plate 192 temperature at two different setpoints, 39° C and 44° C. The second setpoint is set high to permit the heater plate 192 to attain 44° C. temperature, thereby permitting more rapid warming of samples to 39° C. The common terminal of resistors 436, 438 is coupled to the base of a transistor 440, the emitter of which is coupled to +5 VA and the collector of which is coupled through a resistor to the − input terminal of operational amplifier 426. A series resistive voltage divider including a resistor 442 and a resistor 444 is coupled between the output terminal of operational amplifier 426 and ground. The common terminal of resistors 442, 444 is coupled to an analog input terminal X3 of multiplexer 332. Heater control circuit 322 operating status is thus multiplexed into μC 284. Additionally, heater control status, as reflected by the voltage at the collector of transistor 434, controls the flow of current through the heater foil 182. This is accomplished through a transistor 446, the base of which is coupled to the collector of transistor 434 and the collector of which is coupled to the − HEATER terminal, 196-2, of connector 196. The + HEATER terminal, 196-1, of connector 196 is coupled to + VUNREGulated. The emitter of transistor 446 is coupled through a parallel resistance network to ground. The base of transistor 446 is also coupled through two series diodes to ground, which limits the current through the heater foil to approximately 0.4 A. The − THermistor terminal, 196-4, of connector 196 is coupled to ground.

Terminal P1.6 of μC 284 is coupled through a type LL4148 diode to the − input terminal of a type LM324A operational amplifier 450 in the sample port circuit 326. The + input terminal of operational amplifier 450 is coupled to VREF. The output terminal of operational amplifier 450 is coupled to the base of a type BC848C NPN transistor 452, the emitter of which is coupled through a 100 KΩ feedback resistor to the − input terminal of operational amplifier 450 and to ground through 60 Ω resistance, which limits the current through the sample port LED at a constant current. The collector of transistor 452 is coupled to terminal 168-1 of the sample port connector 168. +5 VA is coupled to terminal 168-2, the VDD terminal, of connector 168. VUNREGulated is coupled to terminal 168-5 of connector 168. The SAMPle IN terminal, 168-4, of connector 168 is coupled to ground through a 20 KΩ, 1% resistor and through a 0.01 μF capacitor to the − input terminal of a type LPC662IM operational amplifier 456. The + input terminal of operational amplifier 456 is coupled to ground. The output terminal of operational amplifier 456 is coupled through a parallel RC feedback circuit including a 200 KΩ, 1% resistor and a 39 μF capacitor to its − input terminal. The output terminal of operational amplifier 456 is coupled through a 0.0047 μF capacitor to the + input terminal of a type LPC662IM operational amplifier 458. The + input terminal of operational amplifier 458 is coupled to ground through a 15 KΩ, 1% resistor.

The − input terminal of operational amplifier 458 is coupled to ground through a 20 KΩ, 1% resistor. The output terminal of operational amplifier 458 is coupled to the cathode of a type LL4148 diode, the anode of which is coupled through a 100 KΩ, 1% resistor to the − input terminal of operational amplifier 458. The output terminal of operational amplifier 458 is also coupled to the anode of a type LL4148 diode 460, the cathode of which is coupled through a 1 MΩ, 1% resistor 462 to the − input terminal of operational amplifier 458. This provides a hysteresis-type configuration which has different gains depending upon whether the voltage at the + input terminal of operational amplifier 458 is greater than or less than the voltage at the − input terminal thereof. The common terminal of diode 460 and resistor 462 is coupled through the series combination of a 1 KΩ, 1% resistor 464 and a 0.047 μF capacitor 466 to ground. The common terminal of resistor 464 and capacitor 466 is coupled to the SAMPle DETect input terminal, X7, of multiplexer 332.

Terminal P1.7 of μC 284 is coupled through two series resistors in the magnet control circuit 328 to ground. The common terminal of these resistors is coupled to the base of a transistor 470, the emitter of which is coupled to ground. The collector of transistor 470 is coupled through series resistors to +5 VA. The common terminal of these resistors is coupled to the base of a transistor 471, the emitter of which is coupled to +5 VA and the collector of which is coupled to the − input terminal of an operational amplifier 472. The series combination of a resistor 474 and a resistor 476 is coupled between VREF and ground. A capacitor is coupled across resistor 476. The common terminal of resistors 474 and 476 is coupled to the + input terminal of operational amplifier 472.

The output terminal of operational amplifier 472 is coupled to the base of a magnet coil 144-driver transistor 478. The emitter of transistor 478 is coupled through a resistor to ground, which limits the current through the magnet coil at a constant current, and through a feedback resistor to the − input terminal of operational amplifier 472. A capacitor is coupled between the − input terminal of operational amplifier 472 and ground. The collector of transistor 478 is coupled to terminal 156-3 of connector 156. Terminal 156-1 of connector 156 is coupled to VUNREGulated. Coil 144 is coupled across connectors 156-1 and 156-3. The series combination of a resistor and a capacitor is also coupled across connectors 156-1 and 156-3. A flyback diode is also coupled across terminals 156-1 and 156-3.

The bar code LED driver circuit 330 which is associated with photodiode 224 includes eight Stanley type BR1102W bar code-illuminating LEDs 484-1–484-8. The anode of LED 484-1 is coupled to +5 V and its cathode is coupled to the Anode terminal of optical switch 486. Optical switch 486 provides the source and detector for flag 264 to indicate when the strip adapter top and bottom assemblies 130, 132 are closed together. The collector terminal, C, of optical switch 486 is coupled to InPut terminal 3 of ASIC 290, and through a 100 KΩ load resistor to +5 V. The cathode terminal, K, of optical switch 486 is coupled through a 120 Ω load resistor to the collector of a type BC848C NPN transistor 490-1, the emitter of which is coupled to ground and the base of which is coupled through a 10 KΩ resistor to OutPut terminal 17 of ASIC 290. The anodes of the remaining LEDs 484-2–484-8 are coupled through a common 60 Ω load resistance to +5 V. The cathodes of LEDs 484-2–484-8 are coupled to the collectors of type BC848C NPN transistors 490-2–490-8, respectively. The emitters of transistor 490-2–490-8 are coupled to ground. The bases of transistor 490-2–490-8 are coupled through respective 10 KΩ resistors to OutPut terminals 16–10, respectively, of ASIC 290.

LEDs 484-1–484-8 are mounted on PCB 114 and emit light through respective slit openings 204-1–204-8, respectively. LED's 484-1–484-8 are sequentially energized through transistors 490-1–490-8, respectively. The presence or absence of a bar code in region 492 of a particular test strip 101 placed in instrument 100 is sensed by transmission of light from a respective LED 484-1–484-8 by conduction of photodiode 224. This identifies certain test strip 101 lot-specific parameters for instrument 100.

In operation, a sample 514 is deposited in the test strip 101 sample well 494 over location 210. Radiation from LED 164, which is strobed at 0.25 sec. intervals, detected by photodiode 166 establishes the dosing of strip 101. START LED 238 is strobed at 50 msec. intervals until the arrival of the sample 514 at the region of strip 101 over START LED 238 is established by the radiation from START LED 238 detected by photodiode 242. The flow time of the sample 514 between the sample application point at well 494 and the detection of the arrival of the sample 514 over the START LED 238 establishes the sample 514 as blood or a control. The control solutions, being less viscous, flow between these two locations more rapidly, and this is detected by the instrument 100. The minimum flow time that the instrument 100 will interpret as blood and/or the maximum flow time that the instrument 100 will interpret as control can be varied from strip lot to strip lot by changing (a) parameter(s) in the user-insertable EEPROM key 119. This relieves the user from the need to indicate to the instrument 100 or otherwise record when a quality control check is being conducted.

After photodiode 242 has detected the arrival of the sample 514 over the START LED 238, the START LED 238 is deenergized and the FILL LED 240 is energized. The next decrease in radiation detected by photodiode 242 indicates the arrival of the sample 514 over the FILL region of the strip 101. The elapsed time between detection by photodiode 242 of arrival of the sample 514 over START LED 238 and detection by photodiode 242 of arrival of the sample 514 over FILL LED 240 is used by the instrument 100 to determine whether the volume of the sample 514 which was applied is adequate to conduct a coagulation test. If the instrument 100 determines that the applied sample 514 volume was inadequate to conduct a test, the instrument 100 provides an error message and returns to its ready state. If the instrument 100 determines that the applied sample 514 volume was sufficient to conduct a coagulation time test reliably, FILL LED 240 is deenergized and MAIN assay LED 244 is energized. Electromagnet 140 is also energized and monitoring by photodiode 242 of MAIN assay LED 244 radiation begins. Magnet assembly 140, when driven by magnet current control circuit 328, stirs ferromagnetic particles from the test strip 101 borne by the sample 514, be it blood or control. The particles reorient themselves along the combined lines of force of magnet assembly 140 and bias magnet 154 and provide a modulated light transmission profile of the sample. This transmission profile, illustrated in FIG. 16 at 500, is detected by photodiode 242 and is multiplexed (DETect–AC1-DC) via multiplexer 332 and A/D 324 into µC 284. Coagulation of the sample causes the reduction in the modulation in this transmission profile as described in U.S. Pat. Nos. 4,849,340 and 5,110,727. Waveform 500 is rectified and the envelope 502 of the rectified waveform 500 is formed.

To reduce the likelihood of double dosing the strip 101, the ratio of START to FILL time-to-sample application to START time is formed. This ratio is compared to a parameter provided from key 119. The ratio must be less than the parameter. Otherwise the instrument 100 will conclude that the strip 101 has been double dosed and will generate an error message. Double dosing is to be avoided because it can refluidize the ferromagnetic particles, producing an erroneous coagulation time reading.

FIGS. 17a–b are much-enlarged fragmentary longitudinal sectional views of a strip 101 taken along section lines 17—17 of FIG. 4. Generally, in the absence of liquid blood, a blood fraction or control (FIG. 17a), the indices of refraction of the strip bottom 506 and top 508 and the air-filled sample volume 510 between them are such that the level of light from LED 164 returning to photodiode 166 is relatively higher. This is illustrated at region 512 of FIG. 18. A liquid sample 514, be it blood, a blood fraction or a control, is deposited into the sample well 494 of strip 101 and migrates into region 510 of strip 101 over region 211 of instrument 100. Owing generally to the matching of the strip bottom 506's, top 508's and liquid 514's indices of refraction and absorption in the case of clear liquids, and generally to absorption and scattering effects in the case of whole blood, a relatively lower light level is detected by photodiode 166 as illustrated at region 522 in FIG. 18 when a liquid is present on strip 101 adjacent region 211. This optical detection scheme permits a clear control to be used.

Figure 19:
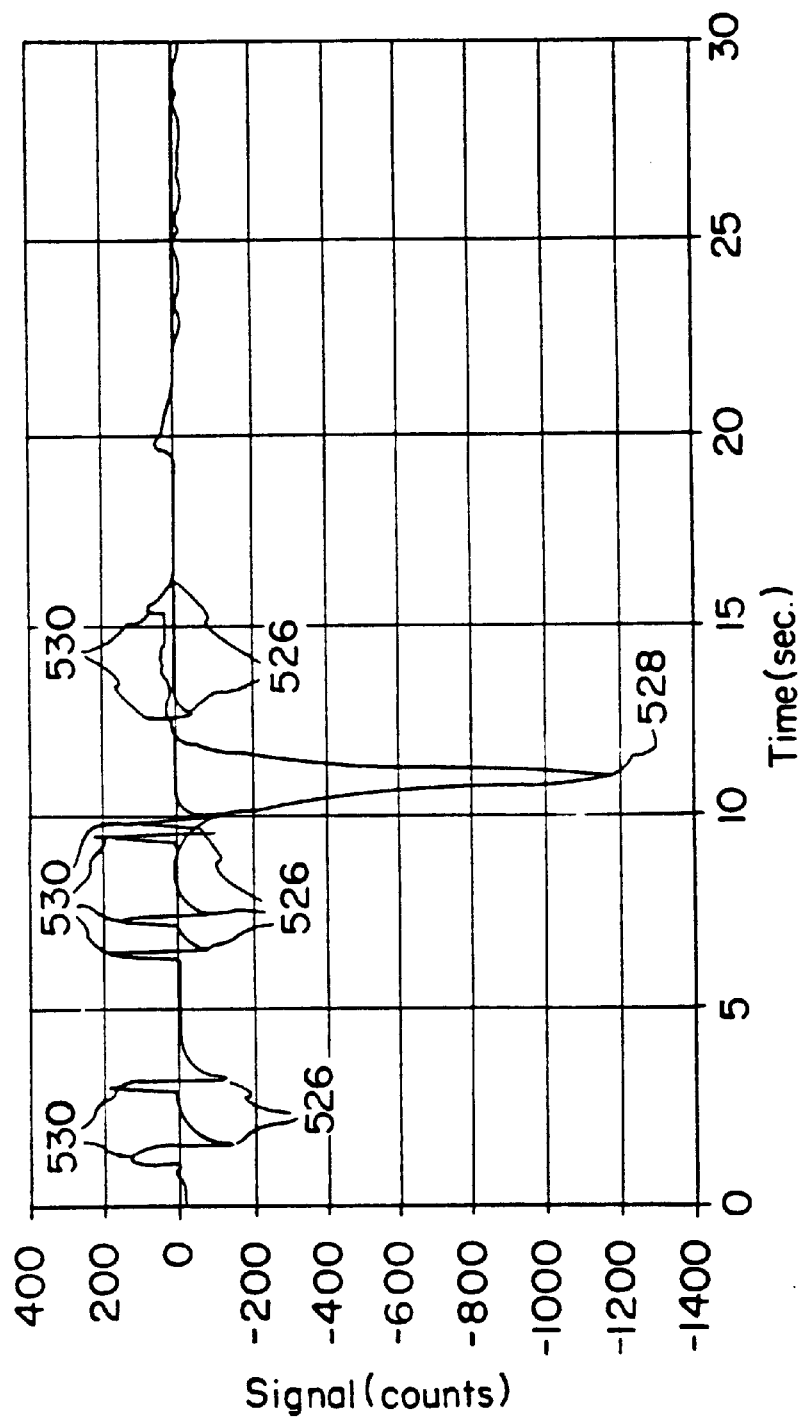

FIG. 19 illustrates two waveforms useful in understanding the start noise immunization technique employed in an instrument according to the present invention. It has been experimentally determined that, unless provisions are made in instrument 100 to prevent it, instrument 100 can be falsely triggered by negative-going noise spikes 526 that are generated during application of a sample to a test strip 101. Such spikes 526 are caused when the user accidentally taps or moves the strip 101 from side to side or in and out of the optics assembly 116 during sample application. Such negative-going spikes 526 can be greater than the instrument 100's -60 mV starting threshold, but are typically shorter in duration than the negative-going start signal 528 and are preceded or followed immediately by positive-going spikes 530. This is in contrast to the actual liquid sample signal 528 which is only negative-going. This difference is used to discriminate effectively between signal 528 and noise 526, 530. The instrument 100's START algorithm discriminates between short (noise) 526, 530 and long (start signal) 528 duration signals using negative trend, rate of signal change and negative threshold criteria. The flow of the START algorithm includes the following illustrative characteristics: three consecutive data points sampled 50 msec apart must be negative relative to a reference and have rates of signal change more negative than –7.3 mV/50 msec (–30 counts of the A/D converted input signal at 0.243 mV/count) with an absolute signal change more negative than the –60 mV (–246 counts) instrument 100 start threshold. The parameters stored in the EEPROM 119 then would include a signal delta of –30 counts and a start threshold of –246 counts.

What is claimed is:

1. In combination, an instrument for determining a characteristic of a biological fluid or a control comprising a radiation-reflective surface, a first source for irradiating the surface, and a first detector for detecting radiation reflected from the surface, and a cuvette for holding a sample of the biological fluid or control the characteristic of which is to be determined, the cuvette having two opposed walls substantially transparent to the source radiation and reflected radiation, the first source and first detector being disposed adjacent a first one of said two opposed walls and the radiation reflective surface being disposed adjacent a second of said two opposed walls, a second source for irradiating the surface, the first detector detecting radiation from the second source reflected from the surface, the second source positioned to transmit radiation through said two opposed walls for reflection by the surface and transmission back through said two opposed walls to the first detector to indicate whether a sample has reached a first point in the cuvette, the cuvette further including a region for bearing a code, the instrument further comprising one or more third radiation sources for irradiating the code bearing region, one or more second detectors for detecting the transmission of radiation through the code bearing region, the third radiation source or sources and second detector or detectors mounted adjacent the code bearing region to detect the code, the insturment further including a heater for maintaining the biological fluid or control at a desired temperature, means for mounting the heater adjacent the surface, means for providing power to the heater and means for monitoring the surface temperature and for feeding the monitored temperature back to the means for providing power to the heater, the heater comprising an electrically resistive foil, the surface comprising a first radiation reflective surface of a tile, the tile further comprising a second surface opposite the first surface thereof, and means for mounting the electrically resistive foil to the second surface of the tile.

2. The combination of claim 1, wherein the instrument further comprises a fourth source for irradiating the cuvette and a third detector for detecting when a sample has been applied to a sample application point in the cuvette, the third detector detecting radiation from the fourth radiation source transmitted through one of said two opposed walls of the cuvette, reflected and transmitted back through said one wall to the third detector.

3. In combination, an instrument for determining a characteristic of a biological fluid or a control comprising a radiation-reflective surface, a first source for irradiating the surface, and a first detector for detecting radiation reflected from the surface, and a cuvette for holding a sample of the biological fluid or control the characteristic of which is to be determined, the cuvette having two opposed walls substantially transparent to the source radiation and reflected radiation, the first source and first detector being disposed adjacent a first one of said two opposed walls and the radiation reflective surface being disposed adjacent a second of said two opposed walls, the cuvette comprising a region for bearing a code, the instrument further comprising multiple second radiation sources for irradiating the code bearing region, a second detector for detecting the transmission of radiation through the code bearing region, the second radiation sources and second detector mounted adjacent the code bearing region to detect the code, the second detector having an active region which extends adjacent the code bearing region to detect the transmission of radiation from all of said second radiation sources, and means for activating the second radiation sources in a predetermined sequence to permit the detection and determination of the code borne by the code bearing region, a user-insertable key having non-volatile memory containing data representative of instrument operating parameters, a port for receiving the key, means for comparing the code to the data representative of instrument operating parameters contained on the user-insertable key, and means for disabling the instrument if the comparison of the code and the data representative of instrument operating parameters contained on the user-insertable key is unfavorable.

4. The combination of claim 3 wherein the instrument further comprises a third source for irradiating the cuvette and a third detector for detecting when a sample has been applied to a sample application point in the cuvette, the third detector detecting radiation from the third radiation source transmitted through one of said two opposed walls of the cuvette, reflected and transmitted back through said one wall to the third detector.

5. In combination, an instrument for determining a characteristic of a biological fluid or a control comprising a radiation-reflective surface, a first source for irradiating the surface, and a first detector for detecting radiation reflected from the surface, and a cuvette for holding a sample of the biological fluid or control the characteristic of which is to be determined, the cuvette having two opposed walls substantially transparent to the source radiation and reflected radiation, the first source and first detector being disposed adjacent a first one of said two opposed walls and the radiation reflective surface being disposed adjacent a second of said two opposed walls, a second source for irradiating the surface, the first detector detecting radiation from the second source reflected from the surface, the second source positioned to transmit radiation through said two opposed walls for reflection by the surface and transmission back through said two opposed walls to the first detector to indicate whether a sample has reached a first point in the cuvette, the cuvette comprising a region for bearing a code, the instrument further comprising one or more third radiation sources for irradiating the code bearing region, one or more second detectors for detecting the transmission of radiation through the code bearing region, the third radiation source or sources and second detector or detectors mounted adjacent the code bearing region to detect the code, a user-insertable key having non-volatile memory containing data representative of instrument operating parameters, a port for receiving the key, means for comparing the code to the data representative of instrument operating parameters contained on the user-insertable key, and means for disabling the instrument if the comparison of the code and the data representative of instrument operating parameters contained on the user-insertable key is unfavorable.

6. The combination of claim 5 wherein the instrument further comprises a fourth source for irradiating the cuvette and a third detector for detecting when a sample has been applied to a sample application point in the cuvette, the third detector detecting radiation from the fourth radiation source transmitted through one of said two opposed walls of the cuvette, reflected and transmitted back through said one wall to the third detector.

7. In combination, an instrument for determining a characteristic of a biological fluid or a control comprising a radiation-reflective surface, a first source for irradiating the surface, and a first detector for detecting radiation reflected from the surface, and a cuvette for holding a sample of the biological fluid or control the characteristic of which is to be determined, the cuvette having two opposed walls substantially transparent to the source radiation and reflected radiation, the first source and first detector being disposed adjacent a first one of said two opposed walls and the radiation reflective surface being disposed adjacent a second of said two opposed walls, a second source for irradiating the surface, the first detector detecting radiation from the second source reflected from the surface, the second source positioned to transmit radiation through said two opposed walls for reflection by the surface and transmission back through said two opposed walls to the first detector to indicate whether a sample has reached a first point in the cuvette, the cuvette comprising a region for bearing a code, the instrument further comprising multiple third radiation sources for irradiating the code bearing region, a second detector for detecting the transmission of radiation through the code bearing region, the third radiation sources and second detector mounted adjacent the code bearing region to detect the code, the second detector having an active region which extends adjacent the code bearing region to detect the transmission of radiation from all of said third radiation sources, and means for activating the third radiation sources in a predetermined sequence to permit the detection and determination of the code borne by the code bearing region, a user-insertable key having non-volatile memory containing data representative of instrument operating parameters, a port for receiving the key, means for comparing the code to the data representative of instrument operating parameters contained on the user-insertable key, and means for disabling the instrument if the comparison of the code and the data representative of instrument operating parameters contained on the user-insertable key is unfavorable.

8. The combination of claim 7, wherein the instrument further comprises a fourth source for irradiating the cuvette and a third detector for detecting when a sample has been applied to a sample application point in the cuvette, the third detector detecting radiation from the fourth radiation source transmitted through one of said two opposed walls of the cuvette, reflected and transmitted back through said one wall to the third detector.

* * * * *